US010314922B2

(12) United States Patent
Han et al.

(10) Patent No.: US 10,314,922 B2
(45) Date of Patent: Jun. 11, 2019

(54) TRIMALEIMIDE LINKERS AND USES THEREOF

(71) Applicant: NewBio Therapeutics, Inc., Shanghai (CN)

(72) Inventors: Nianhe Han, Shanghai (CN); Deqiang An, Shanghai (CN); Di Zeng, Shanghai (CN); Baoxiang Wang, Shanghai (CN); Hang Yang, Shanghai (CN); Li Jian, Shanghai (CN); Chun Yang, Shanghai (CN)

(73) Assignee: NewBio Therapeutics, Inc., Shanghai (CN)

( * ) Notice: Subject to any disclaimer, the term of this patent is extended or adjusted under 35 U.S.C. 154(b) by 0 days.

(21) Appl. No.: 15/577,536

(22) PCT Filed: May 17, 2016

(86) PCT No.: PCT/CN2016/082287
§ 371 (c)(1),
(2) Date: Nov. 28, 2017

(87) PCT Pub. No.: WO2016/192528
PCT Pub. Date: Dec. 8, 2016

(65) Prior Publication Data
US 2018/0147295 A1 May 31, 2018

(30) Foreign Application Priority Data

May 29, 2015 (CN) .......................... 2015 1 0289369

(51) Int. Cl.
*A61K 47/68* (2017.01)
*C07D 207/452* (2006.01)
*C07K 16/32* (2006.01)

(52) U.S. Cl.
CPC ...... *A61K 47/6889* (2017.08); *A61K 47/6803* (2017.08); *C07D 207/452* (2013.01); *C07K 16/32* (2013.01); *C07K 2317/24* (2013.01)

(58) Field of Classification Search
CPC ............ A61K 47/6889; A61K 47/6803; C07D 207/452; C07K 16/32; C07K 2317/14
USPC ....................................... 530/391.1
See application file for complete search history.

(56) References Cited

FOREIGN PATENT DOCUMENTS

| WO | 2006034488 A2 | 3/2006 |
| WO | 2009000523 A1 | 12/2008 |
| WO | 2014114207 A1 | 7/2014 |

OTHER PUBLICATIONS

Kossmehl, et al., Cross-Linking Reactions on Polyamides by Bis- and Tris(Maleimide)s, Macromolecular Materials and Engineering, 1995, 227(1):139-157.
PCT International Search Report and Written Opinion, PCT/CN2016/082287, dated Aug. 22, 2016.
King, D.J., et al., "Preparation and preclinical evaluation of humanised A33 immunoconjugates for radioimmunotherapy," British Journal of Cancer, 1995, vol. 72; No. 6, pp. 1364-1372.
First Office Action issued in corresponding Japanese Application No. 2018-511321 dated Oct. 2, 2018, 4 pages.

*Primary Examiner* — Kristin A Vajda
(74) *Attorney, Agent, or Firm* — Quarles & Brady LLP

(57) ABSTRACT

A type of trimaleimide linkers and uses thereof are disclosed. The trimaleimide linkers can be applied for preparation of antibody-drug conjugate as shown by formula I: $L\text{-}(T\text{-}A\text{-}D)_n$ I wherein, L is an antibody, antibody fragment or protein; T is a trimaleimide linker; A is a cleavable linker group or a noncleavable linker; D is a drug; n is an integer ranging from 1 to 8.

9 Claims, 6 Drawing Sheets

TRIMALEIMIDE LINKERS AND USES THEREOF

CROSS-REFERENCE TO RELATED APPLICATIONS

This application represents the U.S. national stage entry of International Application No. PCT/CN2016/082287 filed May 17, 2016, which claims priority to Chinese Patent Application No. 201510289369.3 filed May 29, 2015, the disclosure of which is incorporated herein by reference in its entirety and for all purposes.

FIELD OF THE INVENTION

The invention relates to pharmaceutical treatment of tumors or other diseases via antibody-drug conjugates (ADCs). The invention further relates to preparation of ADCs utilizing a specific trimaleimide linker to control the drug/antibody ratio (DAR).

BACKGROUND OF THE INVENTION

Antibody-drug conjugates are a kind of novel targeted therapeutic agents for the treatment of cancer and autoimmune diseases. The basic design philosophy originated from the notions of "magic bullet" and "drug targeting", i.e. delivering drugs to the target region via specific carriers, which was firstly proposed by Paul Ehrlich in 1931. However, restricted by the technologies of antibody and high potency cytotoxic drug, the first ADC drug, Malotarg™ (for the treatment of acute myleocytic leukemia, AML), was not approved by FDA until 2000. Recently, FDA approved two ADC drugs, Adcetris™ (for the treatment of HL/ALCL by Seattle Genetics, 2011) and Kadcyla™ (for the treatment of breast cancer by Genentech, 2013), indicating that the rapid development stage of ADCs for cancer treatment is coming. In traditional ADC structures, highly-potent cytotoxic drugs are normally linked, via different linkers, to the ε-amino group of lysine residues or cysteine residues (after full/partial reduction of interchain disulfide bonds). The optimized DARs are preferred to be 2~4. The large number of ε-amino groups of lysine residues (~80/mAb) and the non-selective conjugation mode lead to the uncertainty of conjugation sites and conjugated drug numbers, and thus afford ADC product with high heterogeneity. For example, T-DM1 (average DAR~3.5) has a DAR distribution ranging from 0 to 8 (Rapid Commun. Mass Spectrom. 2005, 19, 1806-1814). Similarly, when selecting cysteine residues as conjugation sites, although an antibody contains only four reducible inter-chain disulfide bonds, it must be partially reduced and conjugated to give ADCs with preferred average DAR (2~4) (Bioconjugate Chem. 2005, 16, 1282-1290). As generally used reducing agents (DTT, TCEP, etc) couldn't selectively reduce the interchain disulfide bonds, the conjugation products thus obtained are not homogeneous either, containing multi-conjugates with DAR of 0, 2, 4, 6 and 8. Even for a fraction with specific DAR value, it is a mixture that contains conjugates with drugs conjugated at different sites. The heterogeneity of ADC products may ultimately lead to different PK, efficacy, and toxicity properties for different fractions. For example, fractions with higher DAR have, in some cases, been reported to clear more rapidly and contributed to more severe toxicity (Bioconjugate Chem. 2011, 22, 1994-2004).

To overcome the above mentioned shortcomings of traditional linker technologies, new linker technology is highly needed to provide site-specific conjugation products.

SUMMARY OF THE INVENTION

The invention disclosed innovative trimaleimide linkers that could be used to produce ADCs via chemical coupling methods.

In the first aspect, the invention provides antibody-drug conjugate of formula I:

$$L\text{-}(T\text{-}A\text{-}D)_n \qquad \qquad I$$

wherein: L is an antibody, antibody fragment, or protein; T is a trimaleimide linker; A is other linker part, D is a cytotoxic drug, n is an integer ranging from 1 to 8.

The trimaleimide linker has the structure of formula II:

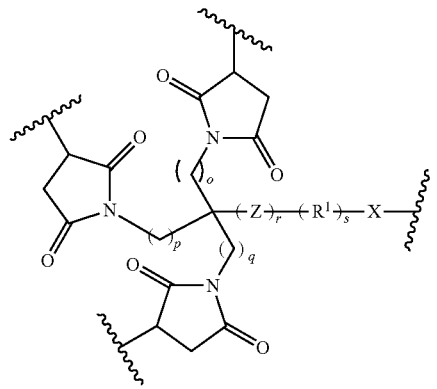

wherein: Z is selected from O, S, $NR^2$, $NR^3C(=O)$, $C(=O)NR^4$, $C(=O)O$, $OC(=O)$, $C(=S)O$, $OC(=S)$, $C(=S)NR^5$, $NR^6C(=S)$, $C(=S)S$, $SC(=S)$, $NR^7C(=O)NR^8$, $NR^9C(=S)NR^{10}$, $OC(=O)NR^{11}$, or $NR^{12}C(=O)O$; $R^1$ is selected from alkylene, alkenlene, alkynylene, arylene, $-(CH_2CH_2O)_t-$, $-(OCH_2CH_2)_w-$, or any combination thereof, wherein t and w are independently selected from integers ranging from 1 to 18; $R^2$, $R^3$, $R^4$, $R^5$, $R^6$, $R^7$, $R^8$, $R^9$, $R^{10}$, $R^{11}$ and $R^{12}$ are independently selected from H, alkyl, aryl, heterocyclyl, aryl, or heteroaryl; r is selected from 0 or 1; s is an integer ranging from 0 to 8; X is selected from $NR^{13}$, O, S, $C(=O)$, $C(=S)$, $C(=O)NR^{14}$, $NR^{15}C(=O)$, $NR^{16}C(=S)$, $C(=S)NR^{17}$, $OC(=O)$, $C(=O)O$, $OC(=S)$, or $C(=S)O$; wherein $R^{13}$, $R^{14}$, $R^{15}$, $R^{16}$ and $R^{17}$ are independently selected from H, alkyl, aryl, heterocyclyl, arylalkyl, or heteroarylalkyl; o, p and q are integers independently selected from 0 to 8, including 0, 1, 2, 3, 4, 5, 6, 7, and 8, wherein when one of them is set to zero, the others cannot be zero.

In a preferred embodiment, A is cleavable linker combination or noncleavable linker; preferably, A has formula III or IV:

$$C\text{-}E_e\text{-}F_f \qquad \qquad III$$

$$G_g \qquad \qquad IV$$

wherein: C is a cleavable linker; E and F are self-immolative linker; e and f are independently selected from integers ranging from 0 to 5, including 0, 1, 2, 3, 4 and 5; G is a noncleavable linker; g is an integer ranging from 0 to 5, including 0, 1, 2, 3, 4 and 5.

In another preferred embodiment, the invention provides antibody-drug conjugate of formula V or VI:

V

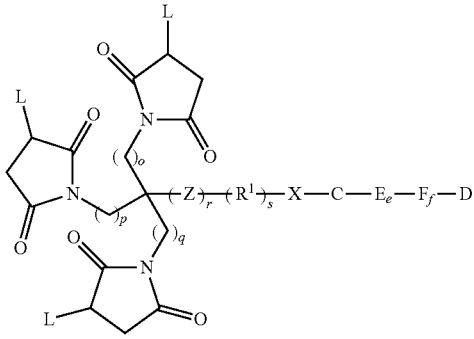

VI

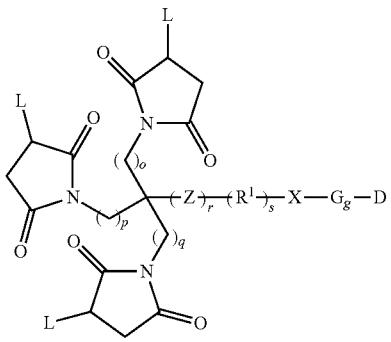

wherein: L is an antibody, antibody fragment, or protein; Z is selected from O, S, $NR^2$, $NR^3C(=O)$, $C(=O)NR^4$, $C(=O)O$, $OC(=O)$, $C(=S)O$, $OC(=S)$, $C(=S)NR^5$, $NR^6C(=S)$, $C(=S)S$, $SC(=S)$, $NR^7C(=O)NR^8$, $NR^9C(=S)NR^{10}$, $OC(=O)NR^{11}$, or $NR^{12}C(=O)O$; $R^1$ is selected from alkylene, alkenlene, alkynlene, arylene, —($CH_2CH_2O$)$_t$—, —($OCH_2CH_2$)$_w$—, or any combination thereof, wherein t and w are integers independently selected from 1 to 18; $R^2$, $R^3$, $R^4$, $R^5$, $R^6$, $R^7$, $R^8$, $R^9$, $R^{10}$, and $R^{11}$ and $R^{12}$ are independently selected from H, alkyl, aryl, heterocyclyl, aryl, or heteroaryl; r is selected from 0 or 1; s is an integer ranging from 0 to 8; X is selected from $NR^{13}$, O, S, $C(=O)$, $C(=S)$, $C(=O)NR^{14}$, $NR^{15}C(=O)$, $NR^{16}C(=S)$, $C(=S)NR^{17}$, $OC(=O)$, $C(=O)O$, $OC(=S)$, or $C(=S)O$; wherein $R^{13}$, $R^{14}$, $R^{15}$, $R^{16}$ and $R^{17}$ are independently selected from H, alkyl, aryl, heterocyclyl, arylalkyl, or heteroarylalkyl; o, p and q are integers independently selected from 0 to 8, wherein when one of them is set to zero, the others cannot be zero.

In another preferred embodiment, antibody is referred to an antibody that targets a receptor or tumor-related antigen on cell surface.

In another preferred embodiment, the drug is referred to cytotoxic, anti-autoimmune or anti-inflammation drug.

In the second aspect, the invention provides trimaleimide linkers of formula 1-10:

| Compound | No. |
|---|---|
| 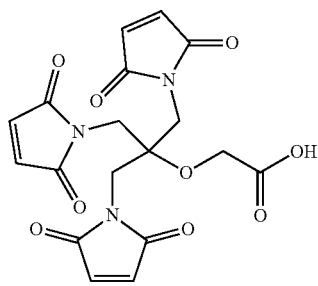 [SMILES: O=C(O)COC(CN1C(=O)C=CC1=O)(CN1C(=O)C=CC1=O)CN1C(=O)C=CC1=O] | 1 |
| 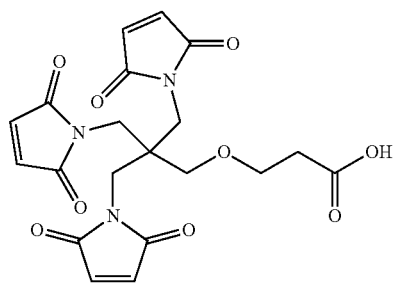 [SMILES: O=C(O)CCOCC(CN1C(=O)C=CC1=O)(CN1C(=O)C=CC1=O)CN1C(=O)C=CC1=O] | 2 |

-continued
| Compound | No. |
|---|---|
| 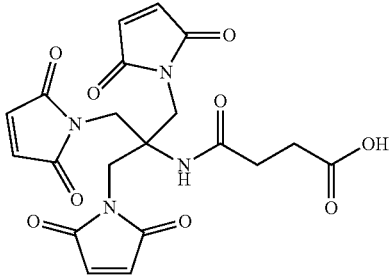 [SMILES: O=C(O)CCC(=O)NC(CN1C(=O)C=CC1=O)(CN1C(=O)C=CC1=O)CN1C(=O)C=CC1=O] | 3 |
| 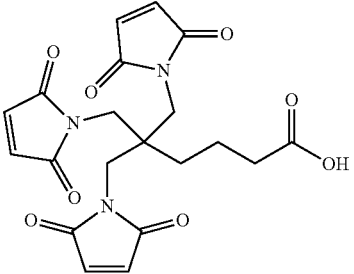 [SMILES: O=C(O)CCCC(CN1C(=O)C=CC1=O)(CN1C(=O)C=CC1=O)CN1C(=O)C=CC1=O] | 4 |
| 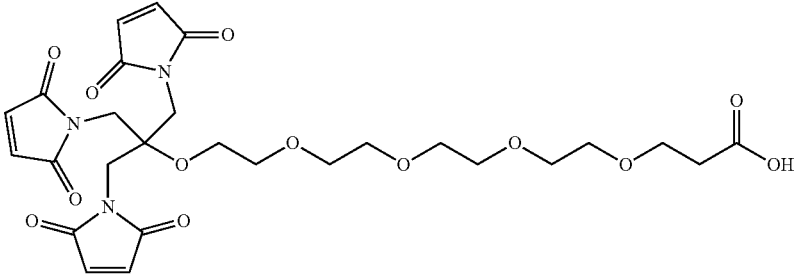 [SMILES: O=C(O)CCOCCOCCOCCOCCOC(CN1C(=O)C=CC1=O)(CN1C(=O)C=CC1=O)CN1C(=O)C=CC1=O] | 5 |
| 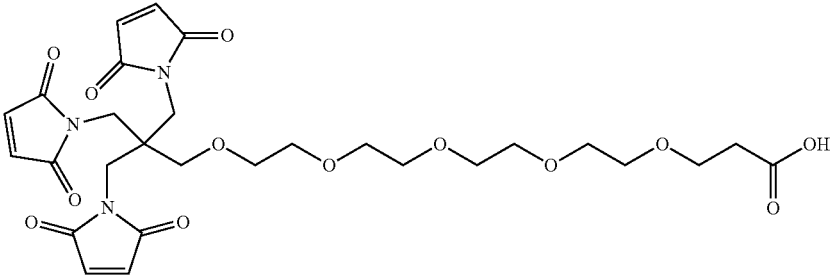 [SMILES: O=C(O)CCOCCOCCOCCOCCOCC(CN1C(=O)C=CC1=O)(CN1C(=O)C=CC1=O)CN1C(=O)C=CC1=O] | 6 |
| 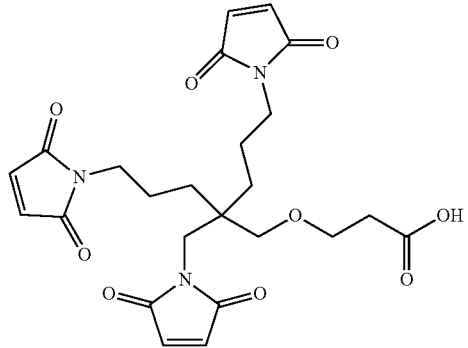 [SMILES: O=C(O)CCOCC(CCCN1C(=O)C=CC1=O)(CCCN1C(=O)C=CC1=O)CN1C(=O)C=CC1=O] | 7 |

| Compound | No. |
|---|---|
| | 8 |
| | 9 |
| | 10 |

In the third aspect, the invention provides the use of a trimaleimide linker of formula VII for manufacturing an antibody-drug conjugate:

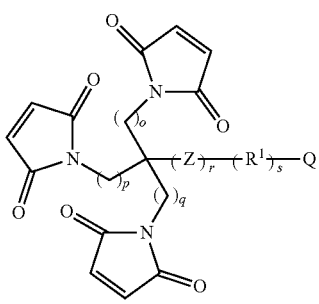

wherein: Z is selected from O, S, $NR^2$, $NR^3C(=O)$, $C(=O)NR^4$, $C(=O)O$, $OC(=O)$, $C(=S)O$, $OC(=S)$, $C(=S)NR^5$, $NR^6C(=S)$, $C(=S)S$, $SC(=S)$, $NR^7C(=O)NR^8$, $NR^9C(=S)NR^{10}$, $OC(=O)NR^{11}$, or $NR^{12}C(=O)O$; $R^1$ is selected from alkylene, alkenlene, alkynlene, arylene, $-(CH_2CH_2O)_t-$, $-(OCH_2CH_2)_w-$, or any combination thereof, wherein t and w are independently selected from integers ranging from 1 to 18; $R^2$, $R^3$, $R^4$, $R^5$, $R^6$, $R^7$, $R^8$, $R^9$, $R^{10}$, $R^{11}$ and $R^{12}$ are independently selected from H, alkyl, aryl, heterocyclyl, aryl, or heteroaryl; r is selected from 0 or 1; s is an integer ranging from 0 to 8; Q is selected from $NHR^{13}$, OH, SH, COOH, $C(=S)OH$, $NR^{14}COOH$, $NR^{15}C(=S)OH$, NCO, or NCS; wherein $R^{13}$, $R^{14}$ and $R^{15}$ are independently selected from H, alkyl, aryl, heterocyclyl, arylalkyl, or heteroarylalkyl; o, p and q are integers independently selected from 0 to 8, wherein when one of them is set to zero, the others cannot be zero.

In a preferred embodiment, the invention provides trimaleimide linkers of formula 1-10:

| Compound | No. |
|---|---|
| 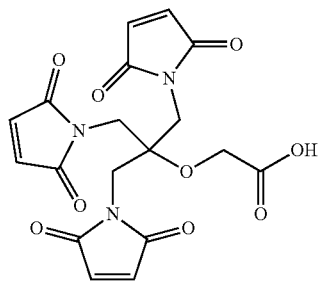 [SMILES: O=C(O)COC(CN1C(=O)C=CC1=O)(CN1C(=O)C=CC1=O)CN1C(=O)C=CC1=O] | 1 |
| 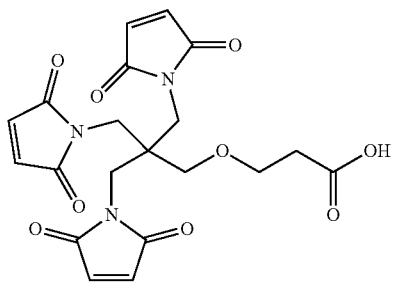 [SMILES: O=C(O)CCOCC(CN1C(=O)C=CC1=O)(CN1C(=O)C=CC1=O)CN1C(=O)C=CC1=O] | 2 |
| 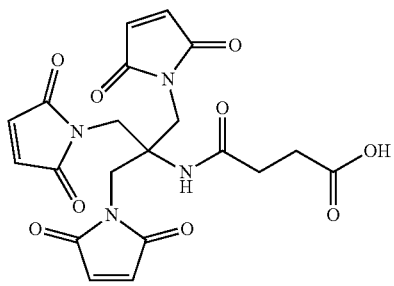 [SMILES: O=C(O)CCC(=O)NC(CN1C(=O)C=CC1=O)(CN1C(=O)C=CC1=O)CN1C(=O)C=CC1=O] | 3 |
| 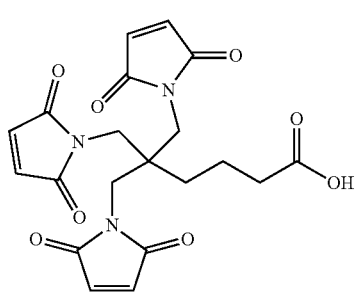 [SMILES: O=C(O)CCCC(CN1C(=O)C=CC1=O)(CN1C(=O)C=CC1=O)CN1C(=O)C=CC1=O] | 4 |

-continued
| Compound | No. |
|---|---|
| 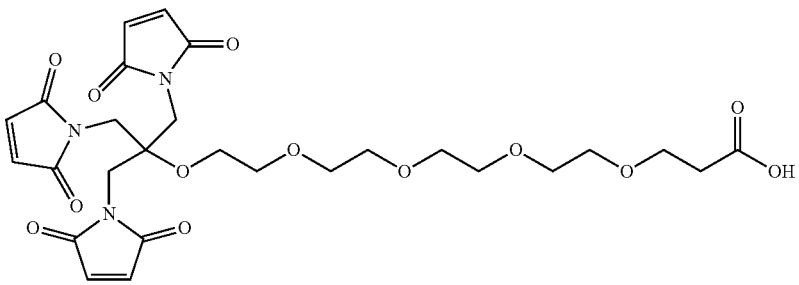 [SMILES: O=C(O)CCOCCOCCOCCOCCOC(CN1C(=O)C=CC1=O)(CN1C(=O)C=CC1=O)CN1C(=O)C=CC1=O] | 5 |
| 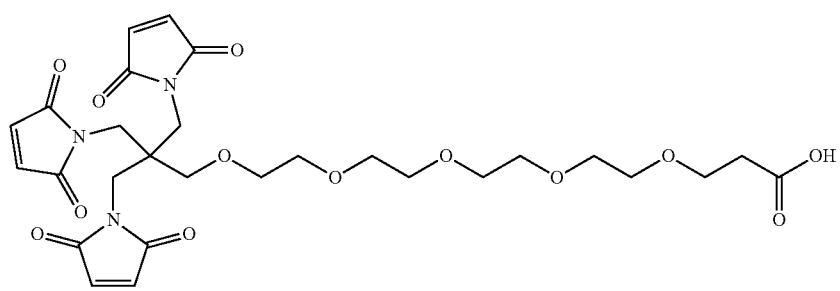 [SMILES: O=C(O)CCOCCOCCOCCOCCOCC(CN1C(=O)C=CC1=O)(CN1C(=O)C=CC1=O)CN1C(=O)C=CC1=O] | 6 |
| 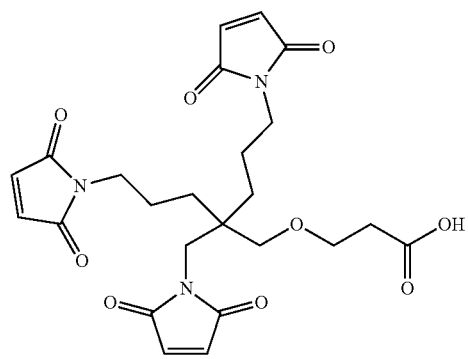 [SMILES: O=C(O)CCOCC(CCCN1C(=O)C=CC1=O)(CCCN1C(=O)C=CC1=O)CN1C(=O)C=CC1=O] | 7 |
| 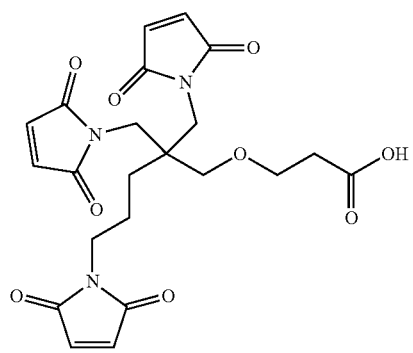 [SMILES: O=C(O)CCOCC(CCCN1C(=O)C=CC1=O)(CN1C(=O)C=CC1=O)CN1C(=O)C=CC1=O] | 8 |

| Compound | No. |
|---|---|
| 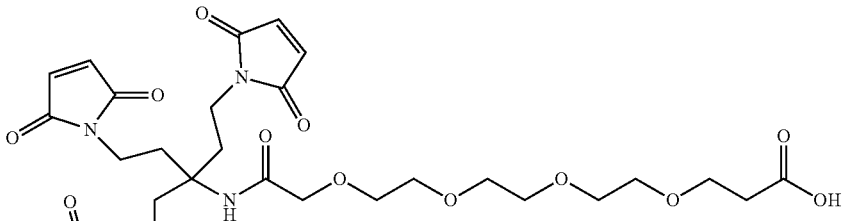 | 9 |
| 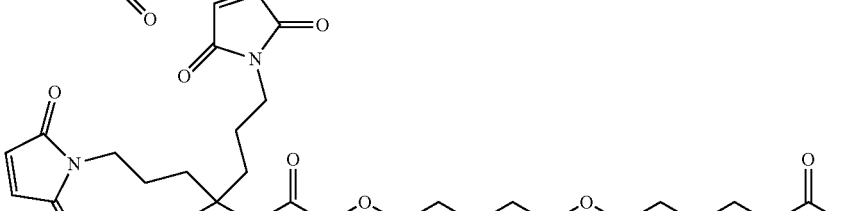 | 10 |

In summary, the invention provides a highly efficient, simple, and practical chemical conjugation method.

ILLUSTRATION

DETAILED DESCRIPTION OF THE INVENTION

Figure 1:
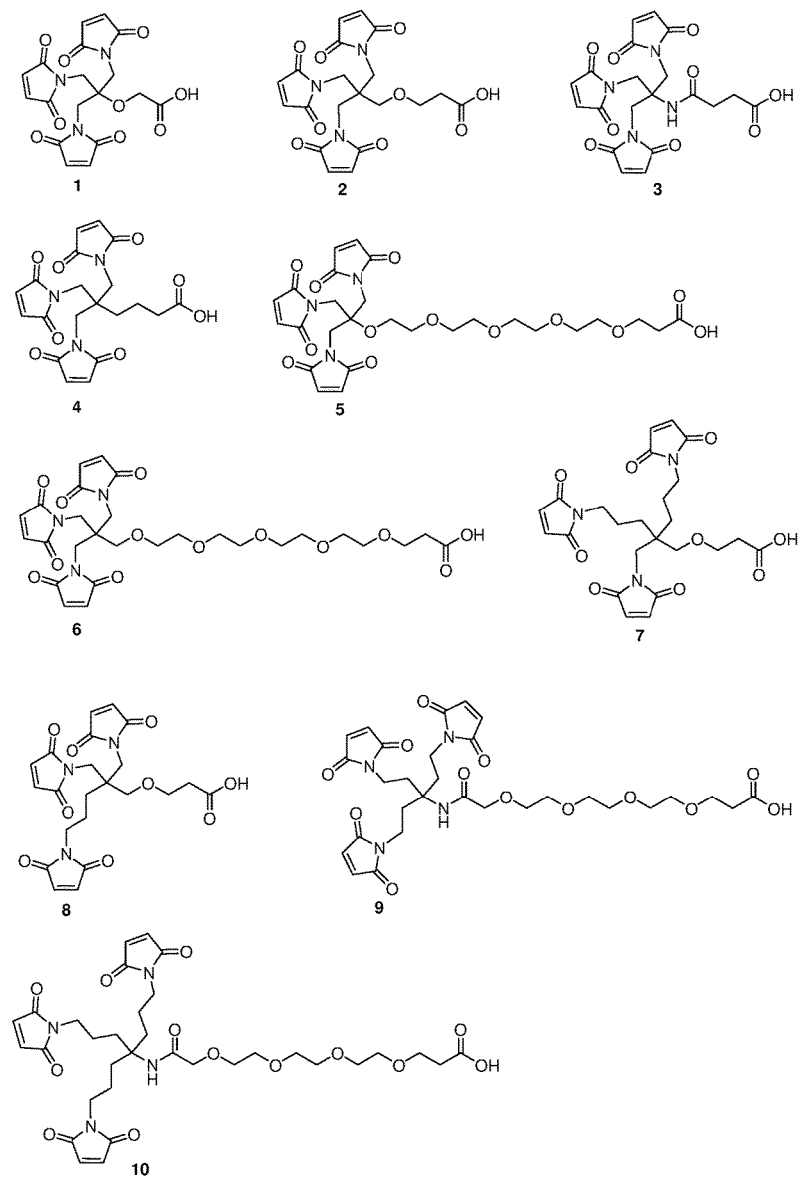
FIG. 1 illustrates the structures of the ten typical trimaleimide linkers disclosed in the invention.
Figure 2:
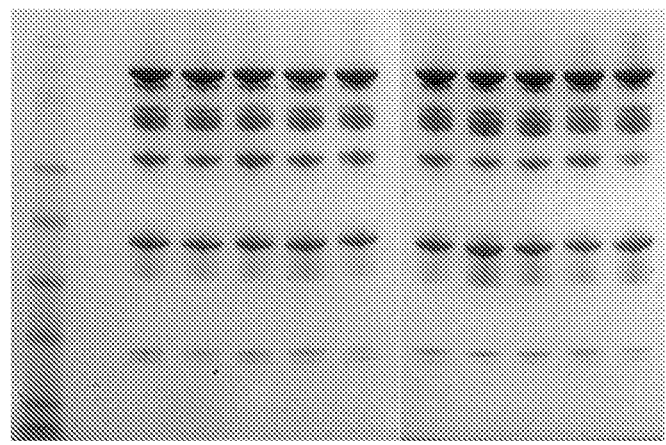
FIG. 2 illustrates the SDS-PAGE results of antibody-drug conjugate of H-trimaleimide linker-vcMMAE, wherein the number 1-10 represents H-1-vcMMAE to H-10-vcMMAE respectively.
Figure 3A:
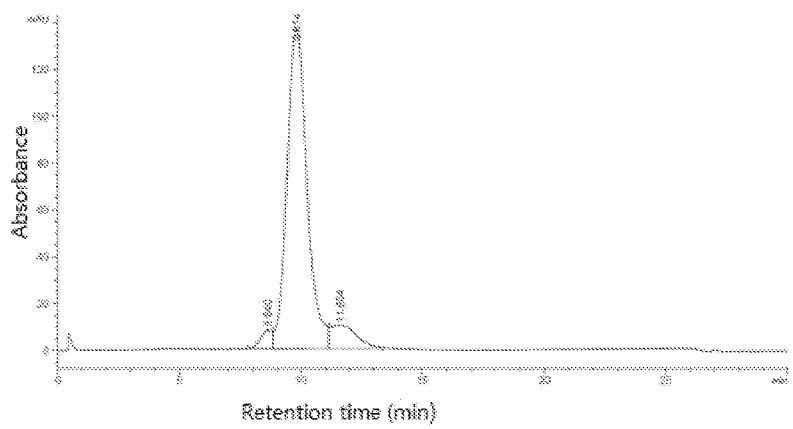
FIG. 3 illustrates the HIC results of antibody-drug conjugate of H-trimaleimide linker-vcMMAE, wherein a is H-2-vcMMAE, b is H-6-vcMMAE.
Figure 3B:
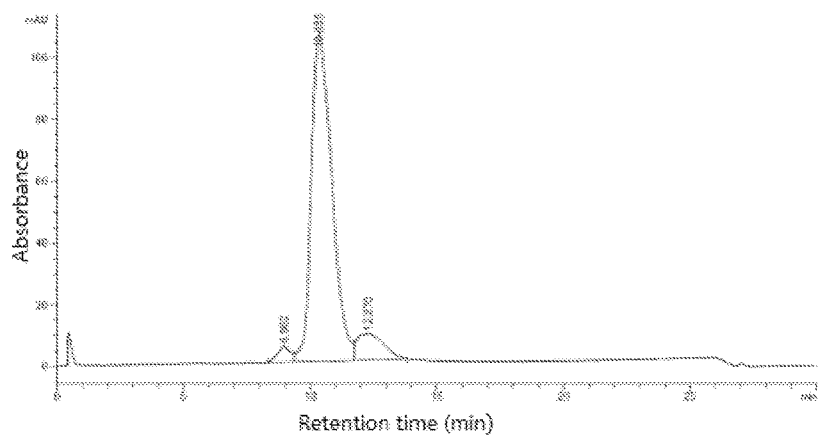
Figure 4A:
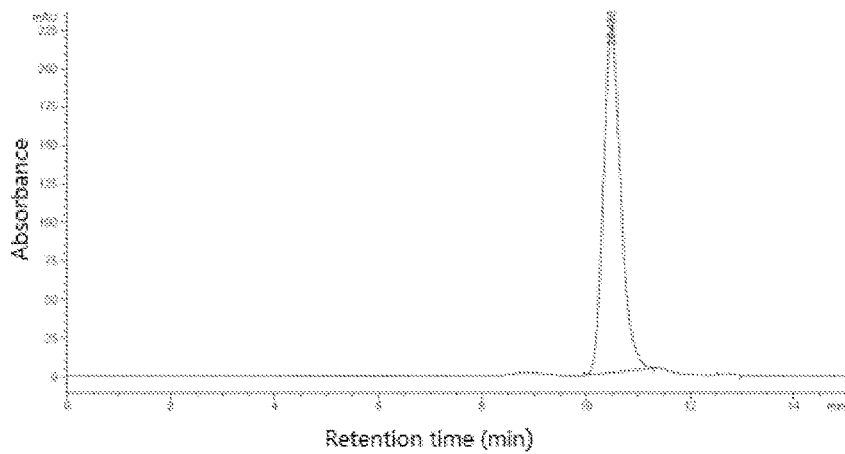
FIG. 4 illustrates the SEC results of antibody-drug conjugate of H-trimaleimide linker-vcMMAE, wherein a is H-2-vcMMAE, b is H-6-M MAE.
Figure 4B:
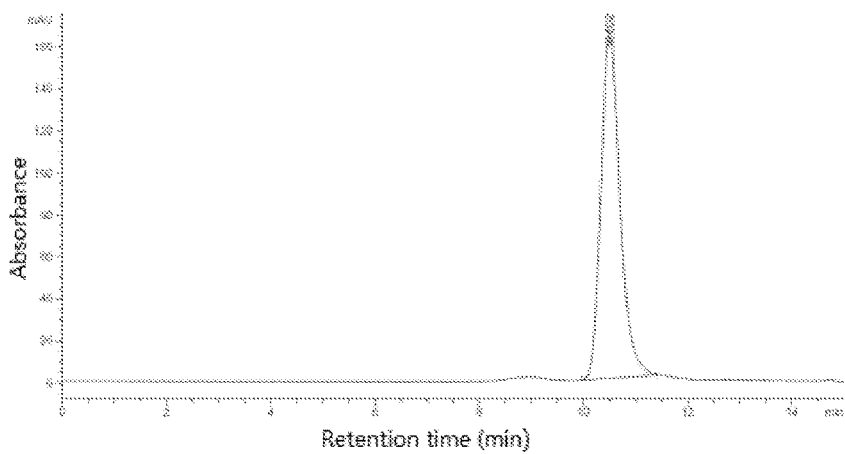

Through extensive study of many years, the inventors developed novel trimaleimide linkers. This type of linkers incorporates three maleimide groups in its structure, which can link to inter-chain cysteine or other amino acid residues within an antibody simultaneously. Conjugation of the trimaleimide linkers with the antibody gives the conjugation product with DAR~3 fraction as the main components (90%+). This type of linkers can be widely used for conjugation with most antibodies, and thus have great application prospect.

Specifically, the "trimaleimide linkers" provided by the invention includes three maleimide groups and a fourth coupling group. The three maleimide groups are used to crosslink antibody interchain thiol (after reduction of interchain disulfide bond) or other groups, while the fourth coupling group is used to link small molecular cytotoxic drug or drug-linker unit:

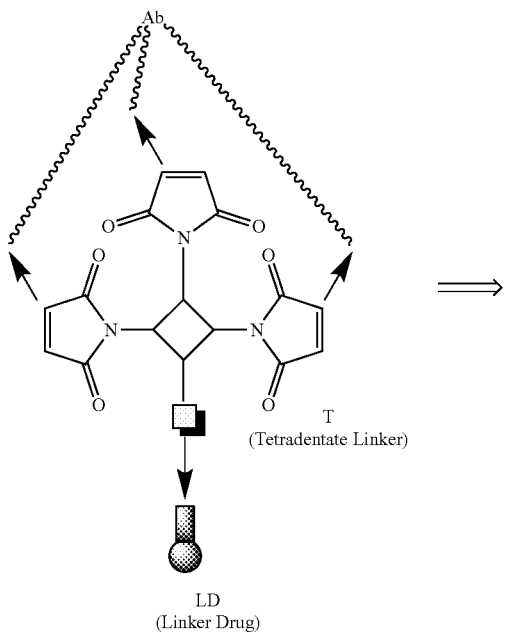

-continued

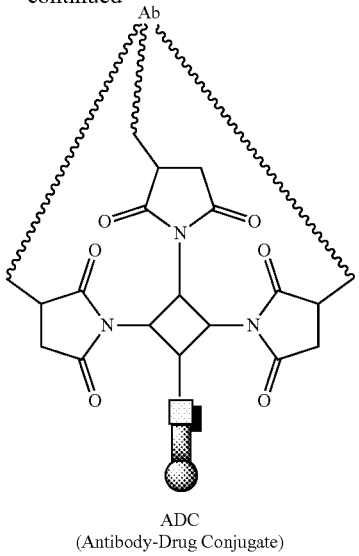

ADC
(Antibody-Drug Conjugate)

The ADCs thus made can be used to selectively deliver cytotoxic drugs to target cell groups, for example, tumor cells. The antibody-drug conjugate will bind specifically to the cell surface proteins, and the binding complex will be internalized rapidly by the cells. Once internalized, the cytotoxic drug will be released in certain active form and take effects. The antibody includes chimeric, humanized, or human antibody; antibody fragment that can bind to antigen; or Fc fused protein; or protein. The drug is highly potent cytotoxic drug, including but not limited to, maytansinoids, auristatins, calicheamicins, doxorubicins, CC-1065 and duocarmycins derivatives, PBD dimers, and tubulysins, etc. Under certain conditions, the drug could be poly(ethylene glycol). The drug itself, or drug-linker units, could be coupled to antibody via trimaleimide linkers, producing inter-chain crosslinked conjugates. Compared to traditional ones, the antibody-drug conjugate provided by the invention has much narrower DAR distribution, with DAR~3 fraction as the main component, and thus greatly improve both structural and pharmacological homogeneities.

Abbreviation

Ab antibody
Ac acetyl
ACN acetonitrile
BOC (Boc) tert-butoxycarbonyl
t-Bu tert-butyl
° C. degree Celsius
DCM dichloromethane
DIEA diisopropylethylamine
DMF N,N-dimethylformamide
ELISA enzyme linked immunosorbent assay
EtOAc ethyl acetate
Eq equivalent
g gram
h hour
HOSu N-hydroxy succinimide
HIC hydrophobic interaction chromatography
HPLC high performance liquid chromatography
LC-MS liquid chromatography-mass spectrum
Linker linker
MeOH methanol
mAb monoclonal antibody
min minute
mL milliliter
MS mass spectrometry
nm nanometer
μg microgram
μL microliter
PE petroleum ether
prep-RP-HPLC preparative-reverse phase-high performance liquid chromatography
rt room temperature
$R_f$ retention time
SDS-PAGE sodium dodecyl sulfate polyacrylamide gel electropheresis
SEC size exclusion chromatography
TEA triethylamine
TFA trifluoroacetic acid
THF tetrohydrofuran
TLC thin layer chromatography
TsCl p-tolyl chloride Definition "Alkyl" is saturated hydrocarbon radical containing normal, secondary, tertiary or cyclic carbon atoms. For example, methyl (—$CH_3$), ethyl (—$CH_2CH_3$), 1-propyl (—$CH_2CH_2CH_3$), 2-propyl (isopropyl, —$CH(CH_3)_2$), and cyclohexyl (—$C_6H_{11}$), etc.

"Alkenyl" is unsaturated hydrocarbon radical containing normal, secondary, tertiary or cyclic carbon atoms with at least one carbon-carbon $sp^2$ double bond. For example, vinyl (—CH=$CH_2$) and allyl (—$CH_2$CH=$CH_2$), etc.

"Alkynyl" is unsaturated hydrocarbon radical containing normal, secondary, tertiary or cyclic carbon atoms with at least one carbon-carbon sp triple bond. For example, ethynyl (—C≡CH) and propargyl (—$CH_2$C≡CH), etc.

"Aryl" is a monovalent aromatic hydrocarbon radical of 6-12 carbon atoms derived by the removal of one hydrogen atom from a single carbon atom of a parent aromatic ring system. For example, phenyl, naphthyl, anthracyl, and biphenyl, etc.

"Heteroaryl" refers to a monovalent aromatic radical derived by the substitution of one or more carbon atoms of a parent aryl radical by one or more hetero atoms selected from N, O, P and S. For example, pyridinyl, thiophenyl, and furanyl, etc.

"Heterocycle" refers to an aromatic or nonaromatic ring system derived by the substitution of one or more carbon atoms of a parent aromatic or nonaromatic ring system by one or more hetero atoms selected from N, O, P, and S. For example, pyridine, thiophene, furan, hexahydropyridine (piperidine), and tetrahydrofuran, etc.

"Heterocyclyl" refers to an aromatic or nonaromatic cyclic radical derived by the removal of one hydrogen atom from a single carbon or hetero atom of a parent heterocycle ring system. For example, pyridinyl, thiophenyl, furanyl, hexahydropyridinyl (piperidinyl), and tetrahydrofuranyl, etc.

"Arylalkyl" refers to an acyclic alkyl radical in which one of the hydrogen atoms bonded to a carbon atom, typically a terminal or $sp^3$ carbon atom, is replaced with an aryl radical. For example, benzyl and 3-phenylpropyl, etc. The alkyl part can also include alkenyl or alkynyl.

"Heteroarylalkyl" refers to an acyclic alkyl radical in which one of the hydrogen atoms bonded to a carbon atom, typically a terminal or $sp^3$ carbon atom, is replaced with a heteroaryl radical. For example, 2-pyridinylethyl and 3-furanylpropyl, etc. The alkyl part of "heteroarylalkyl" can also include alkenyl or alkynyl.

"Alkylene" refers to a saturated, branched or straight chain or cyclic hydrocarbon radical, having two monovalent radical centers derived by the removal of two hydrogen atoms from the same or two different carbon atoms of a parent alkane. For example, methylene (—$CH_2$—), 1,2-ethyl (—$CH_2CH_2$—), and 1,3-propyl (—$CH_2CH_2CH_2$—), etc.

"Alkenylene" refers to an unsaturated, branched or straight chain or cyclic hydrocarbon radical, having two monovalent radical centers derived by the removal of two hydrogen atoms from the same or two different carbon atoms of a parent alkene. For example, 1,2-ethylene (—CH=CH—) and 1,3-propylene (—$CH_2$CH=CH—), etc.

"Alkynlene" refers to an unsaturated, branched or straight chain or cyclic hydrocarbon radical, having two monovalent radical centers derived by the removal of two hydrogen atoms from the same or two different carbon atoms of a parent alkyne. For example, acetylene (—C≡C—) and propargyl (—$CH_2$C≡C—), etc.

"Arylene" refers to aromatic hydrocarbon radical of 6-12 carbon atoms, having two monovalent radical centers derived by the removal of two hydrogen atoms from two different carbon atoms of a parent aromatic ring system. For example, 1,2-phenylene, 1,3-phenylene, and 1,4-phenylene, etc.

"Substituted alkyl", "substituted alkenyl", "substituted alkynyl", "substituted aryl", "substituted heteroaryl", "substituted heterocyclyl", "substituted arylalkyl", and "substituted heteroarylalkyl" refers to, respectively, a radical derived by replacing one or more hydrogen atoms in the corresponding "alkyl", "alkenyl", "alkynyl", "aryl", "heteroaryl", "heterocyclyl", "arylalkyl", and "heteroarylalkyl" radicals, with one or more substitution groups. The substitution groups include, but not limited to, —X, —OR, —$NR_2$, —$NO_2$, —CN, —$SO_3R$, —$CO_2R$, etc. wherein X is halogen atom, R is H, alkyl, aryl, heterocyclyl, protecting group or prodrug. The above-mentioned "alkylene", "alkenylene", and "alkynlene" could also be substituted in a similar way.

"Any combination thereof" refers to a radical derived by connecting two or more radicals in a certain way. For example, benzyl (phenyl+methylene), 3-phenylpropyl (phenyl+1,3-propyl), 2-cyclohexylpropyl (cyclohexyl+1,2-propyl), and 3-(3-pyridinyl)propyl (3-pyridinyl+1,3-propyl), etc.

"Drug/Antibody Ratio, DAR" refers to the number of drugs linked to an antibody molecule. As an ADC product contains components with different DAR, "average DAR" and "DAR distribution" are more convenient parameters for description of the composition of an ADC product. "Average DAR" refers to the ratio of total drug to total antibody molecules, while "DAR distribution" refers to the percentage distribution of different DAR components.

As used herein, "antibody" or "antibody unit" includes within its scope any unit of an antibody that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified.

Antibody comprising the ADCs of the invention preferably retains the antigen binding capability of their native, wild type counterparts. Thus, antibodies of the invention are capable of binding, preferably specifically, to antigens. Such antigens include, for example, tumor-associated antigens (TAA), cell surface receptor proteins and other cell surface molecules, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which an antibody of the invention is capable of binding may be a member of a subset of one of the above-mentioned categories, wherein the other subset(s) of said category comprise other molecules/antigens that have a distinct characteristic (with respect to the antigen of interest).

Antibodies used in ADCs include, but not limited to, antibodies against cell surface receptors and tumor-associated antigens (TAA). Such tumor-associated antigens are known in the art, and can be prepared for use in generating antibodies through methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, Tumor-Associated Antigens (1)-(36) listed below. For convenience, information relating to these antigens, all of which are known in the art, is listed below and includes names, alternative names, Genbank accession numbers. Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references.

Tumor-Associated Antigens (1)-(36):
(1) BMPR1B (bone morephogenetic protein receptor-type IB, Genbank accession no. NM_001203);
(2) E16 (LAT1, SLC7A5, Genbank accession no. NM_003486);
(3) STEAP1 (six transmembrane epithelial antigen of prostate, Genbank accession no. NM_012449);
(4) 0772P (CA125, MUC16, Genbank accession no. AF361486);
(5) MPF (MPF, MSLN, SMR, megakaryocyte potentiating factor, mesothelin, Genbank accession no. NM_005823);
(6) Napi3b (NAPI-3B, NPTIIb, SLC34A2, solute carrier family 34 (sodium phosphate) member 2, type II sodium-dependent phosphate transporter 3b, Genbank accession no. NM_006424);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

(8) PSCA hlg (2700050C12Rik, C530008O16Rik, RIKEN cDNA 2700050C12, RIKEN cDNA 2700050C12 gene, Genbank accession no. AY358628);

(9) ETBR (Endothelin type B receptor, Genbank accession no. AY275463);

(10) MSG783 (RNF124, hypothetical protein FLJ20315, Genbank accession no. NM_017763);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

(12) TrpM4 (BR22450, FLJ20041, TRPM4, TRPM4B, transient receptor potential cation channel, subfamily M, member 4, Genbank accession no. NM_017636);

(13) CRIPTO (CR, CR1, CRGF, CRIPTO, TDGF1, teratocarcinoma-derived growth factor, Genbank accession no. NP_003203 or NM_003212;

(14) CD21 (CR2 (Complement receptor 2) or C3DR (C3d/Epstein Barr virus receptor) or Hs. 73792, Genbank accession no. M26004);

(15) CD79b (CD79B, CD79β, IGb (immunoglobulin associated beta), B29, Genbank accession no. NM_000626);

(16) FcRH2 (IFGP4, IRTA4, SPAP1A (SH2 domain containing phosphatase anchor protein 1a), SPAP1B, SPAP1C, Genbank accession no. NM_030764);

(17) HER2 (ErbB2, Genbank accession no. M11730);

(18) NCA (CEACAM6, Genbank accession no. M18728);

(19) MDP (DPEP1, Genbank accession no. BC017023);

(20) IL20Rα (IL20Ra, ZCYTOR7, Genbank accession no. AF184971);

(21) Brevican (BCAN, BEHAB, Genbank accession no. AF229053);

(22) EphB2R (DRT, ERK, Hek5, EPHT3, Tyro5, Genbank accession no. NM_004442);

(23) ASLG659 (B7h, Genbank accession no. AX092328);

(24) PSCA (Prostate stem cell antigen precursor, Genbank accession no. AJ297436);

(25) GEDA (Genbank accession no. AY260763);

(26) BAFF-R (B-cell activating factor receptor, BLys receptor 3, BR3, Genbank accession no. AF116456);

(27) CD22 (B-cell receptor CD22-β form, Genbank accession no. AK026467);

(28) CD79α (CD79A, CD79α, immunoglobulin-associated alpha, a B-cell specific protein that covalently interacts with Ig beta (CD79B) and forms a complex on the surface with Ig M molecules, transduces a signal involved in B-cell differentiation, Genbank accession No. NP-001774.1);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia, Genbank accession No. NP_001707.1);

(30) HLA-DOB (Beta subunit of MHC class II molecule (Ia antigen) that binds peptides and presents them to CD4+ T lymphocytes, Genbank accession No. NP_002111.1);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability, Genbank accession No. NP_002552.2);

(32) CD72 (B-cell differentiation antigen CD72, Lyb-2, Genbank accession No. NP_001773.1);

(33) LY64 (lymphocyte antigen 64 (RP105), type I membrane protein of the leucine rich repeat (LRR) family, regulates B-cell activation and apoptosis, loss of function is associated with increased disease activity in patients with systemic lupus erythematosis, Genbank accession No. NP_005573.1);

(34) FcRH1 (Fc receptor-like protein 1, a putative receptor for the immunoglobulin Fc domain that contains C2 type Ig-like and ITAM domains, may have a role in B-lymphocyte differentiation, Genbank accession No. NP_443170.1);

(35) IRTA2 (Immunoglobulin superfamily receptor translocation associated 2, a putative immunoreceptor with possible roles in B cell development and lymphomagenesis; deregulation of the gene by translocation occurs in some B-cell malignancies, Genbank accession No. NP_112571.1);

(36) TENB2 (putative transmembrane proteoglycan, related to the EGF/heregulin family of growth factors and follistatin, Genbank accession No. AF179274).

As used herein, the term "drug" or "D" refers to any compound possessing a desired biological activity and a reactive functional group that may be used to incorporate the drug into the conjugate of the invention. The desired biological activity includes the diagnosis, cure, mitigation, treatment, or prevention of disease in man or other animals. Thus, so long as it has the needed reactive functional group, the term "drug" refers to chemicals recognized as drugs in the official United States Pharmacopeia, official Homeopathic Pharmacopeia of the United States, or official National Formulary, or any supplement thereof. Exemplary drugs are set forth in the Physician's Desk Reference (PDR) and in the Orange Book maintained by the U.S. Food and Drug Administration (FDA). New drugs are continually being discovered and developed, and the present invention provides that these new drugs may also be incorporated into a prodrug form of the present invention.

In a preferred aspect of the invention, the drug is: a cytotoxic drug useful in cancer therapy; a protein or polypeptide possessing a desired biological activity, such as a toxin, e.g., abrin, ricin A, pseudomonas exotoxin, and diphtheria toxin; other suitable proteins include tumor necrosis factor, α-interferon, β-interferon, nerve growth factor, platelet derived growth factor, tissue plasminogen activator, and biological response modifiers, such as lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

In one aspect, the drugs are maytansine or maytansinoids. Maytansine compounds inhibit cell proliferation by inhibiting the formation of microtubules of the microtubulin protein, tubulin (Science 1975, 189, 1002-1005; U.S. Pat. No. 5,208,020). Maytansinoids are derivatives of maytansine. Both maytansine and maytansinoids are highly cytotoxic, but their clinical use in cancer therapy has been greatly limited due to poor selectivity for tumors. However, the high cytotoxic potency enables them to be attractive drug moieties in ADCs. The structures shown below are maytansine, maytansinoids, and three representative maytansinoids mostly used in ADC drugs.

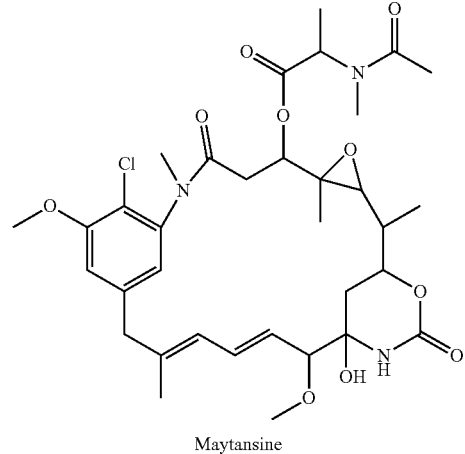
Maytansine

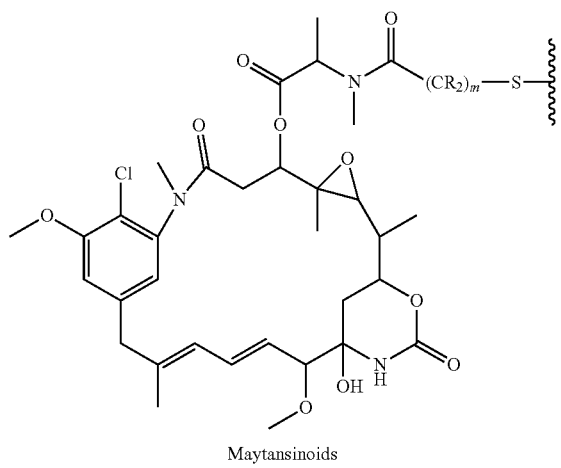
Maytansinoids

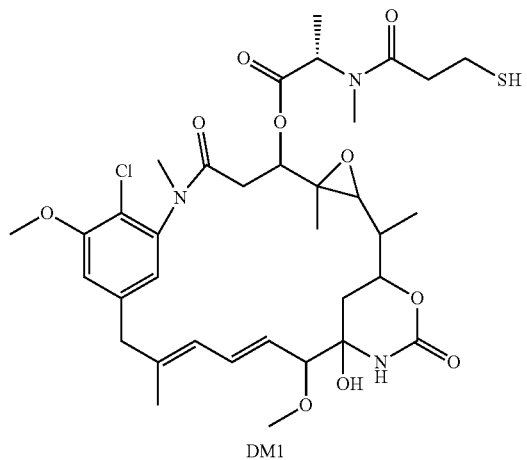
DM1

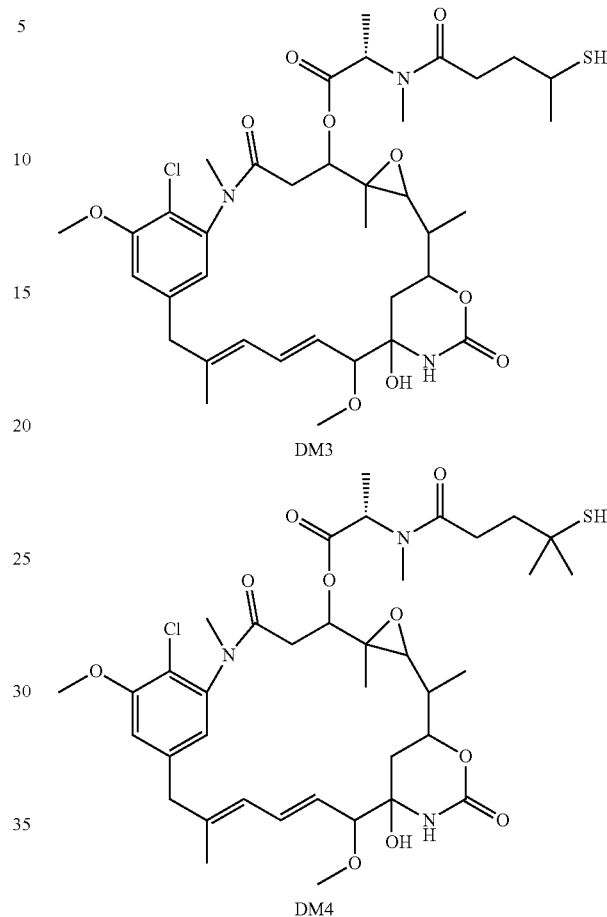
DM3

DM4

The key raw material for preparing maytansinoids is maytansinol, which is obtained from ansamitocins hydrolysis. Ansamitocins could be accessibly produced by fermentation. Ansamitocin derivatives (WO 2012/061590) and alaninyl maytansinol (US 2012/0121615) are also reported to be good candidates as ADC "warheads".

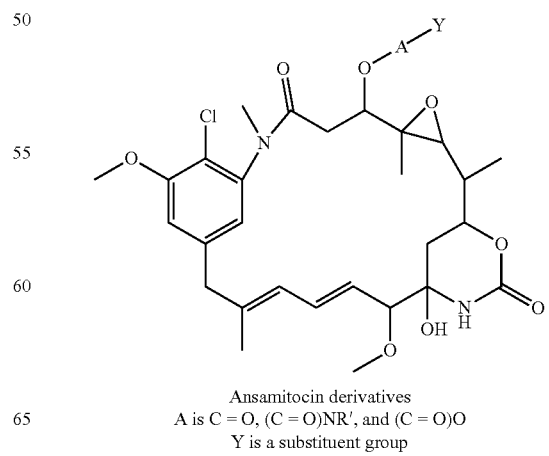
Ansamitocin derivatives
A is C = O, (C = O)NR', and (C = O)O
Y is a substituent group

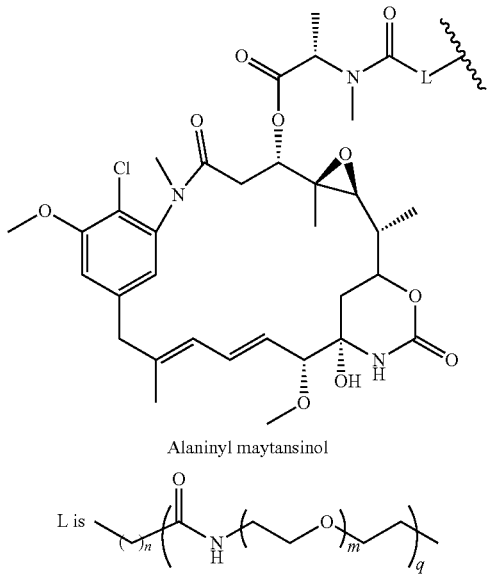

Alaninyl maytansinol

L is
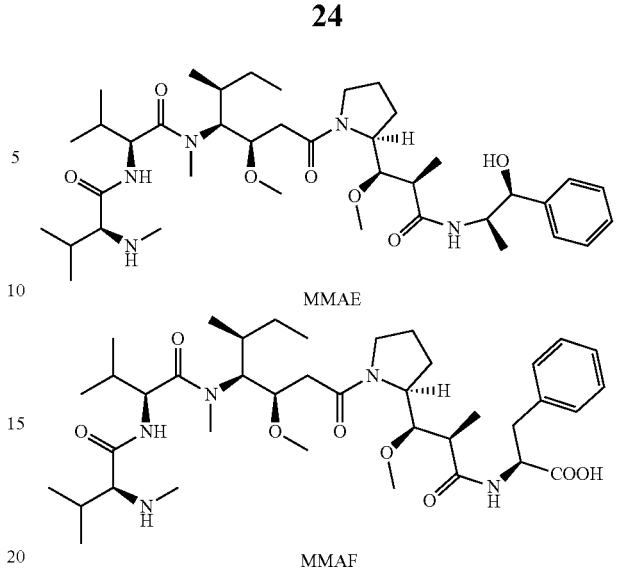

In one aspect, the drugs are auristatins. Auristatins are synthetic analogues of Dolastatin 10, which was isolated from the marine mollusk *Dolabella auricularia* and found to have biological activity (U.S. Pat. No. 7,498,298). Dolastatin 10 is an agent that inhibits tubulin polymerization by binding to the same domain on tubulin as the anticancer drug vincristine. Dolastitin 10, auristatin PE, and auristatin E are all linear peptides having four amino acids, three of which are unique to the dolastatin class of compounds, and a C-terminal amide. Two representative auristatins, monomethyl auristatin E (MMAE) and monomethyl auristatin F (MMAF), are preferred drug moiety candidates for ADCs.

MMAE

MMAF

In one aspect, the drugs are tubulysins. Tubulysins are natural products first isolated from myxobacterial culture, which are potent cell growth inhibitor that act by inhibiting tubulin polymerization, and among which Tubulysin D is the most potent. Tubulysin D is a complex tetrapeptide, and labile in both acidic or basic conditions due to the o-acyl/ N,O-acetal functionality within its structure. US 2011/ 0021568 and US 2013/0224228 disclosed a series of tubulysin analogs, which remove the labile groups and have high cytotoxic potency.

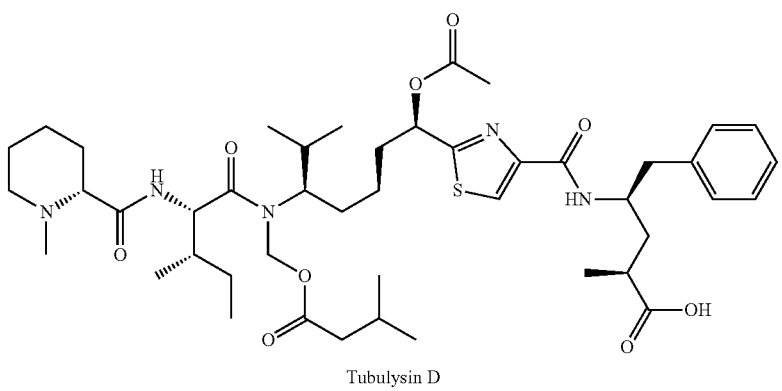

Tubulysin D

In one aspect, the drugs are calicheamicins. Calicheamicins are antitumor antibiotics that bind to the minor groove of DNA and produce site-specific double-strand DNA breaks, causing cell death. Calicheamicins are potent at sub-picomolar concentrations in vitro, but their low therapeutic index precluded further development clinically. The high potency, however, makes them good candidates for ADCs (such as Gemtuzumab Ozogamicin and Inotuzumab Ozogamicin).

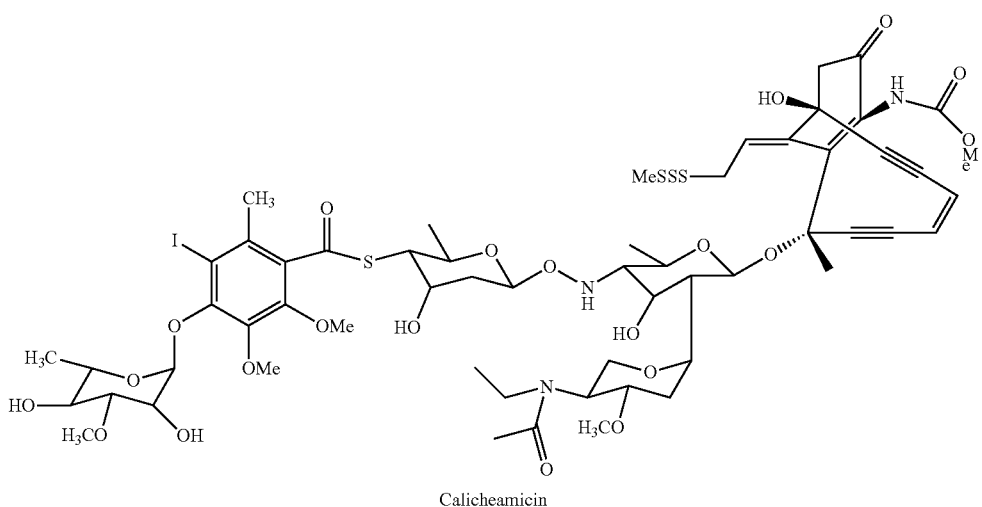

Calicheamicin

In one aspect, the drugs are doxorubicins. Doxorubicin is an intercalating agent that blocks DNA replication and is used as chemotherapeutic agent. Due to the relative low potency of doxorubicin ($IC_{50}$ of 0.1-0.2 μM for human carcinoma lines, whereas subnanomolar activities are now typically seen for ADC payloads), application of doxorubicin as ADC drug moiety is not popular.

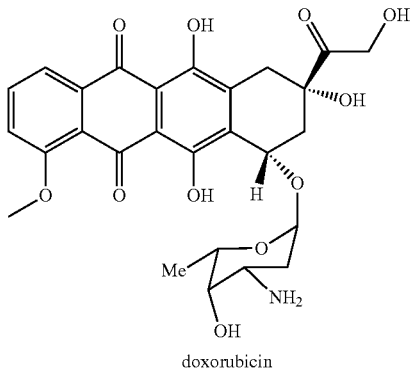 [SMILES: COc1cccc2c1C(=O)c1c(O)c3c(c(O)c1C2=O)C[C@@](O)(C(=O)CO)C[C@@H]3OC1CC(N)C(O)C(C)O1]

doxorubicin

In one aspect, the drugs are duocarmycins, CC-1065 and other cyclopropapyrroloind-4-one (CPI) derivatives, which are potent minor-groove binding DNA alkylating agents. Cyclopropabenzindol-4-one analogues (CBI) are chemically more stable, biologically more potent, and synthetically more accessible than their parent compounds incorporating the nature CPI alkylating subunit. One representative CBI derivative is the phenolic hydroxyl group-protected CBI (see the formula below), which has decreased prodrug toxicity and improved water solubility.

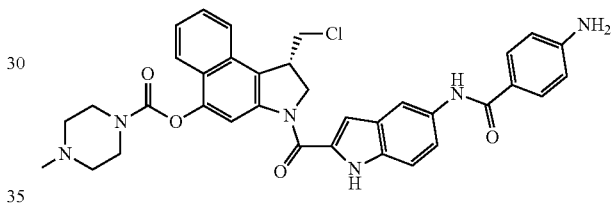

In one aspect, the drugs are pyrrolo[2,1-c][1,4]benzodiazepines (PBDs) or PBD dimers. The pyrrolo[2,1-c][1,4] benzodiazepines (PBDs) are a family of natural products produced by *Streptomyces* species with the unique characteristic of forming nondistortive covalent adducts in the minor groove of DNA specifically at purine-guanine-purine sequences. There is growing interest in using PBDs as part of a small-molecule strategy for targeting DNA sequences and also as novel anticancer and antibacterial agents. (Biochemistry 2008, 47, 11818-11829). The biological activity of these molecules can be potentiated by joining two PBD units together through their C8/C8-hydroxyl functionalities via a flexible alkylene linker (WO 2011/130616). The PBD dimers are thought to form sequence-selective DNA lesions such as the palindromic 5'-Pu-GATC-Py-3' interstrand crosslink, which mainly accounts for their biological activity. These compounds have been shown to be highly useful cytotoxic agents and good candidates as ADC warheads.

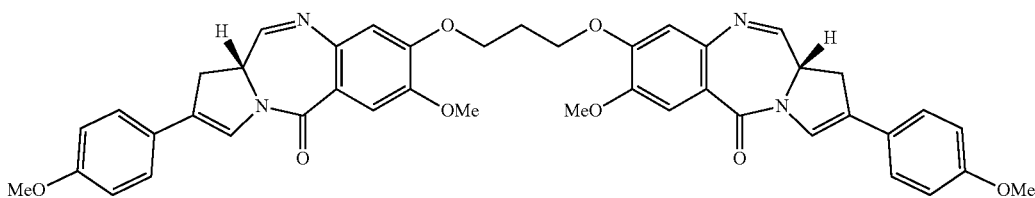

SG2201

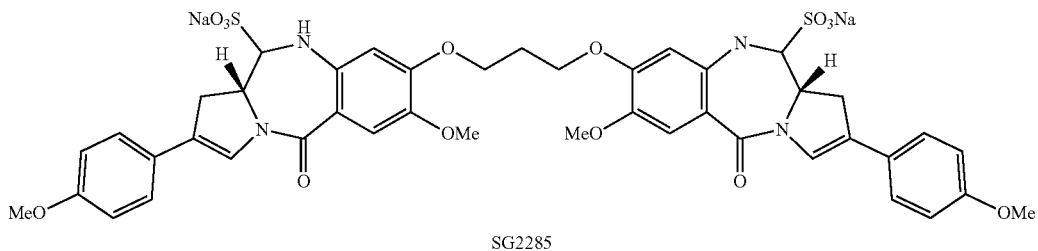

SG2285

In another aspect, the drugs are not limited to above-mentioned categories and include all that could be used in ADCs.

As used herein, the term "linker" or "ADC linker" refers to a bifunctional or multifunctional molecular group that can react with a protein/antibody and a drug respectively, and thus link the protein/antibody to the drug as a "bridge". According to drug release mechanism in cells, linker or ADC linker could be classified into two categories: non-cleavable linker and cleavable linker.

Noncleavable linker is a kind of relatively stable linker, which is difficult to decompose under in-vivo conditions. For ADCs with noncleavable linkers, the release mechanism is believed to occur via internalization of the ADC followed by degradation of the mAb component in the lysosome, resulting in the release of the small molecular drug still attached via the linker to an antibody amino acid residue. The chemical modification of the drug didn't diminish its cytotoxic potential. This form of the drug is, however, charged (amino acid residue) and presumably hard to diffuse into neighboring cells. Hence, it can't kill adjacent tumor cells (bystander effects) that don't express the target antigen (antigen-negative cells) (Bioconjugate Chem. 2010, 21, 5-13). Some common linkers, such as MC linker, MCC linker, etc., are shown as below:

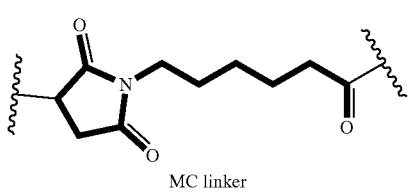

MC linker

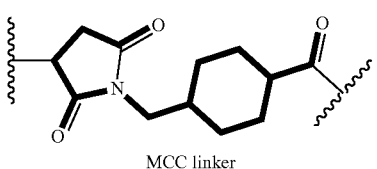

MCC linker

Cleavable linkers, as the name implies, could be cleaved within the target cells that release the active drugs (small molecule drugs themselves). Cleavable linkers can be categorized into two main groups: chemically labile and enzyme-labile linkers.

Chemically labile linkers could be selectively cleaved upon the differential properties between the plasma and some cytoplasmic compartments. Such properties include pH value, glutathione concentration, etc.

For pH sensitive linkers, generally called acid-cleavable linker, the linkers are relatively stable in the blood's neutral environment (pH 7.3-7.5), but will undergo hydrolysis in the mildly acidic endosomes (pH 5.0-6.5) and lysosomes (pH 4.5-5.0). Most of the kinds of linkers, such as hydrozones, carbonates, acetals, ketals, etc., were used for the first generation of ADCs. However, due to the limited plasma stability of the acid-cleavable linkers, the ADCs based on these linkers have relatively short half-life (2-3 days). The low half-lives, to a certain degree, preclude the application of pH-sensitive linkers in the new generations of ADCs to a certain degree.

For glutathione-sensitive linkers, generally called disulfide linkers, the release is attributed to the high intracellular concentration of glutathione in the cytoplasms. (millimolar range) compared to the relatively low concentration in the blood (micromolar range). This is especially true for tumor cells, where the hypoxic state results in enhanced activity of reductive enzymes and therefore even higher glutathione concentrations. Disulfide bonds are thermodynamically stable and thus provide good stability in plasma.

Enzyme-labile linkers are alternative approaches to achieve better control of the drug release, for example, peptide linkers. The peptide linkage will be effectively cleaved by lysosomal proteases, like cathepsin B or plasmin (elevated levels in certain tumor tissues). The peptidic linkages are deemed stable when circulating in plasma, as proteases are normally not active outside cells because of extracellular unfavorable pH and the serum protease inhibitors. Due to the high plasma stability and good intracellular cleaving selectivity and efficiency, enzyme-labile linkers are broadly selected as cleavable linker candidates in ADCs. Typical enzyme-labile linkers include Val-Cit (vc), etc.

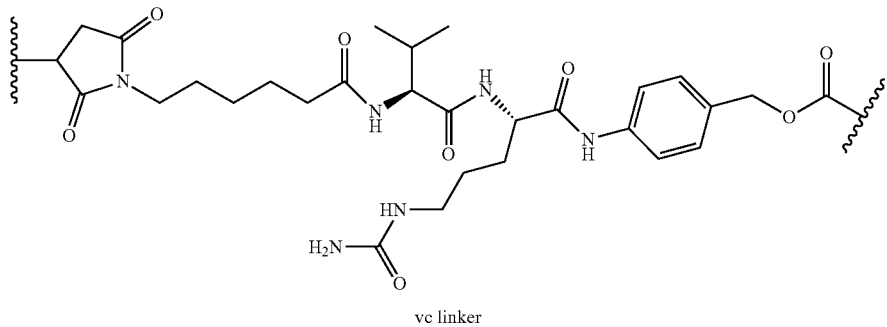 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1]

vc linker

Self-immolative linker is generally sited between cleavable linker and cytotoxic drug, or itself is part of a cleavable linker. The working mechanism of self-immolative linker is that it can undergo self-structural rearrangement to release the linked active drug when the cleavable linker was cut by protease. Typical self-immolative linkers include p-aminobenzyl alcohol (PAB), etc.

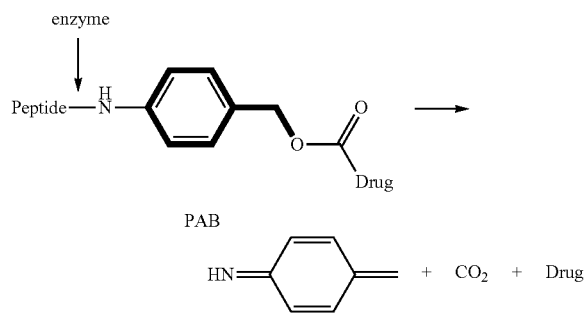

Antibody-Drug Conjugate

The antibody-drug conjugate provided in the invention are composed of antibody, trimaleimide linker, other linker, and drug. Other linker is referred to cleavable linker or non-cleavable linker.

Antibodies are comprised of globular proteins, which have an array of amino acids that have potential linkage sites for drug conjugation. Due to their tertiary and quaternary structure, only solvent-accessible amino acid residues are conjugatable. In practice, high-yielding conjugations to antibodies occur through the ε-amino group of lysine residues or through the sulfhydryl group of cysteine residues.

The abundance of lysine side-chains at the protein surface gives multiple linkage sites for payload conjugation, which leads to a mixture of ADCs with different payload numbers (DARs) and conjugation sites.

In the invention, the conjugation products, albeit still mixture, contain much narrower DAR-spanned products, compared to traditionally produced antibody-drug conjugate. Not only the average DAR is around 3, residing in the optimized ADC DAR range of 2-4, but also the DAR distribution is very narrow, with the DAR~3 fraction as the main component (90%+). In addition, the conjugation products don't contain naked antibody (DAR=0), which have zero payload and thus ineffective for the cell killing. Also, the conjugation products don't contain heavily conjugated antibody (DAR=8), which clears more rapidly than those with low DAR numbers. As a result, the ADC products provided in the invention showed much improved homogeneity.

For trimaleimide linkers, the distance between any two maleimide groups (linker size) may affect the interchain crosslinking between trimaleimide linkers and antibodies. The side chain's (used to link the drugs) length and structure may also affect the ADC property and potency. The inventor synthesized a series of trimaleimide linkers of different sizes to study the above mentioned influence factors.

Trimaleimide Linkers

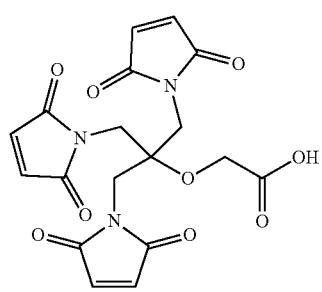

1

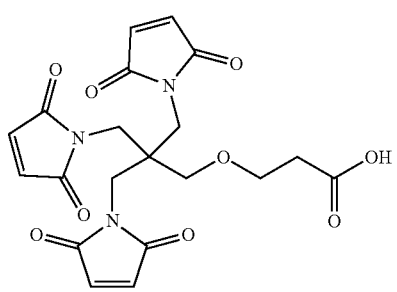

2

-continued
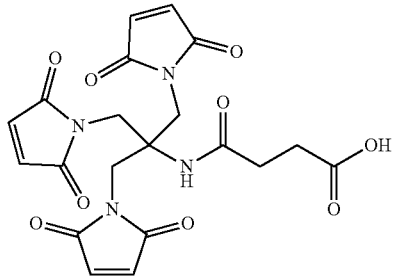
3
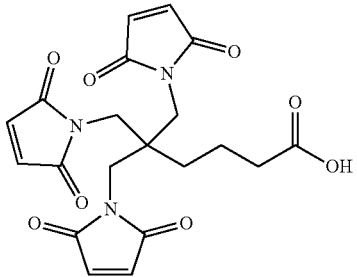
4
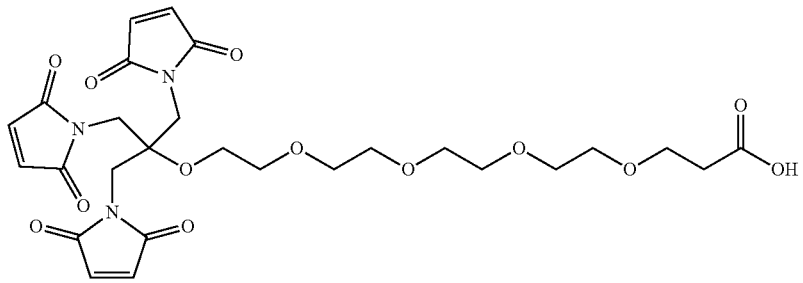
5
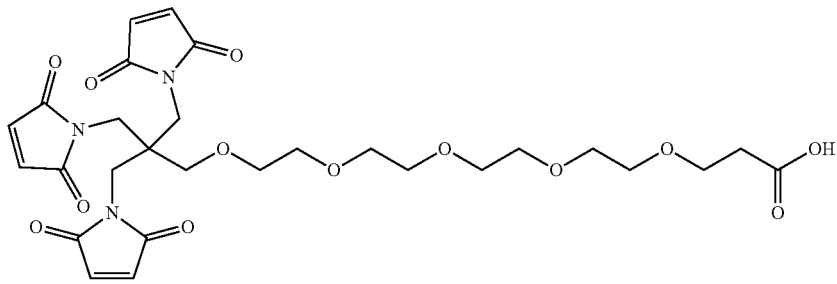
6
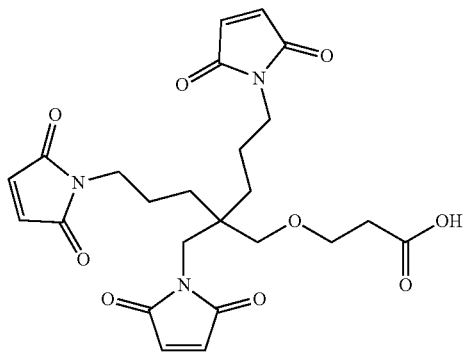
7
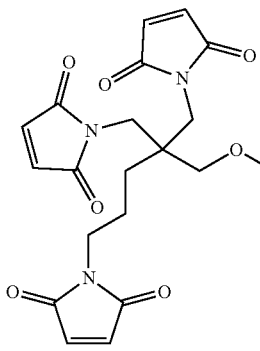
8
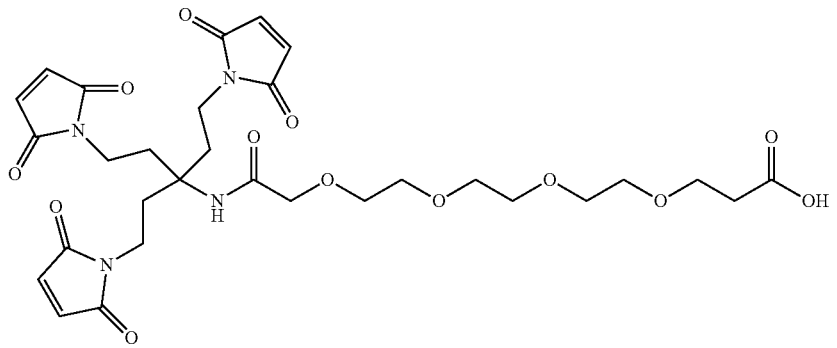
9

-continued

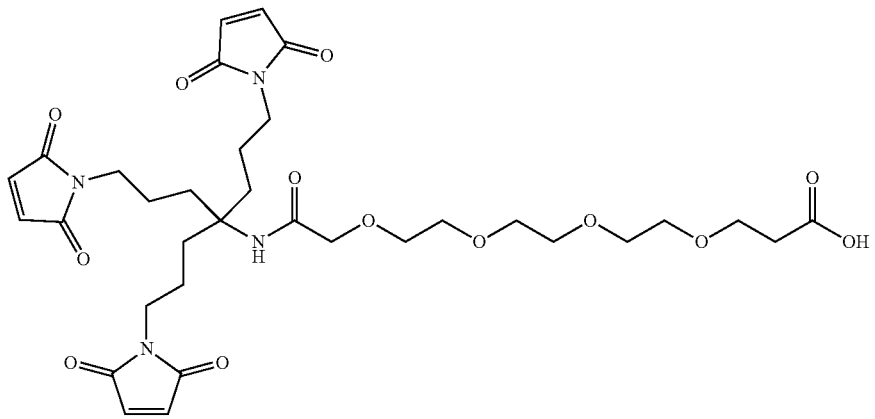

Antibody-Drug Conjugate

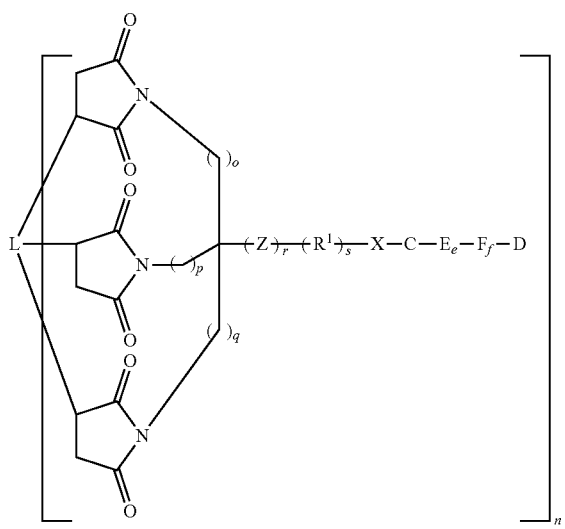

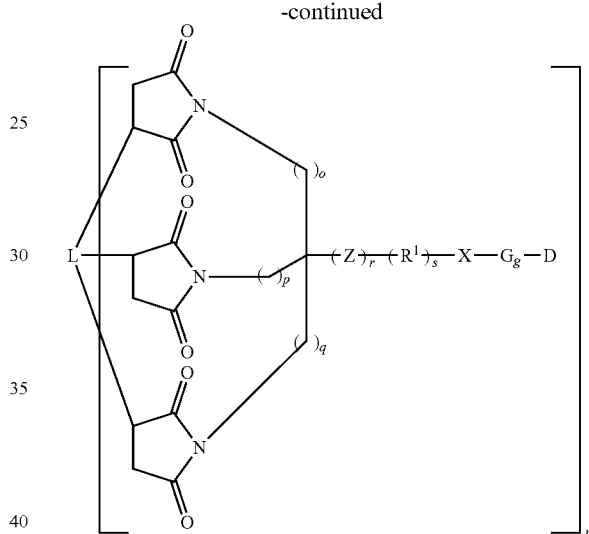

Preparation Method

Method 1: In step A shown below, a linker (L) and a trimaleimide linker (T) were conjugated to afford a trimaleimide linker-linker (T-L). In step B, T-L and a drug (D) were conjugated to give trimaleimide linker-linker-drug (T-L-D). In step C, antibody inter-chain disulfide bonds were selectively reduced to produce a total of eight sulfhydryl groups. In step D, T-L-D crosslinked the sulfhydryl groups to afford inter-chain crosslinked ADCs.

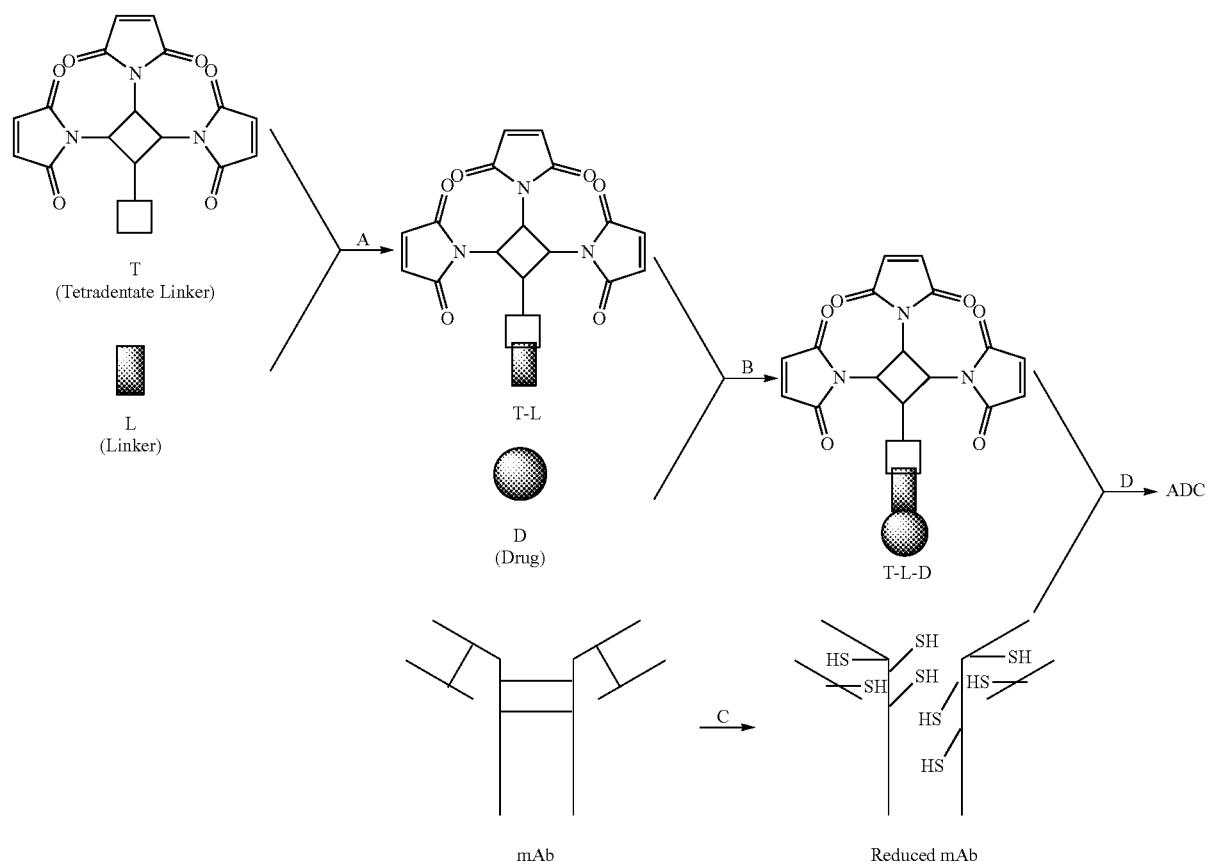

Method 2: In step A shown below, a linker (L) and a drug (D) were conjugated to afford a linker-Drug (L-D). In step B, L-D and a trimaleimide linker (T) were conjugated to give trimaleimide linker-linker-drug (T-L-D). In step C, antibody inter-chain disulfide bonds were selectively reduced to produce a total of eight sulfhydryl groups. In step D, T-L-D crosslinked the sulfhydryl groups to afford inter-chain crosslinked ADCs.

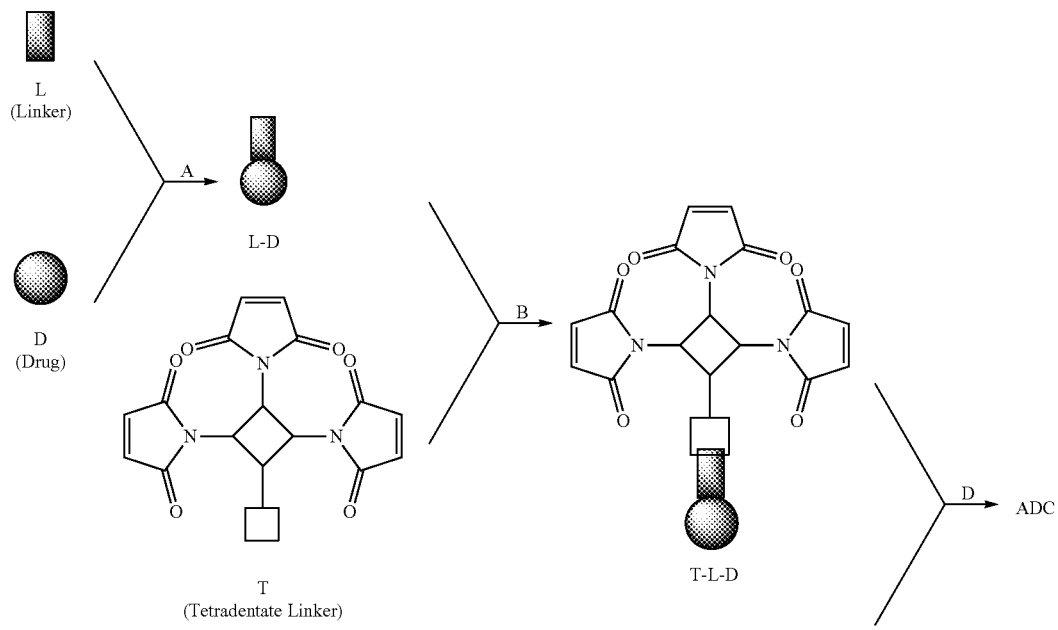

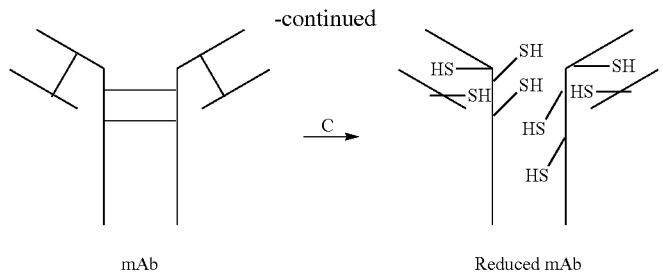

mAb      Reduced mAb

Use

The antibody-drug conjugates provided by the invention target a special cell population and bind to specific cell surface proteins (antigens), followed by the internalization of the complexes into the cell and the drug release within the cell in active forms.

The antibody-drug conjugate provided by the invention target a special cell population, bind to the specific cell surface proteins (antigens), and take effects; or release drugs outside the cell, followed by the diffusion of the drugs into the cell to take effects.

The present invention provides compositions comprising an effective amount of the antibody-drug conjugate and a pharmaceutically acceptable carrier or vehicle.

The present invention provides methods for treatment of cancers or other tumors in animal subjects. The methods are to provide an effective amount of the antibody-drug conjugate provided by the invention to an animal subject with cancers or other tumors.

The present invention provides methods for treatment of autoimmune disease or infectious disease. The methods are to provide an effective amount of the antibody-drug conjugate provided by the invention to an animal subject with autoimmune diseases or infectious diseases.

The above features provided by the present invention, or features provided by examples, can be combined at will. All features provided by the present invention can be applied together with any combination, and each feature can be substituted by any identical, equal, or similar feature. Except for special illustration, all disclosed features are only general examples of the equal or similar features.

The present invention has the following main advantages:
1. The present invention provides, for the first time, the conjugation methods to control the average DAR~3 for the ADC products;
2. The conjugation methods provided by the invention are applicable to most antibodies, which can avoid complicated antibody engineering used to introduce specific sites for coupling. Therefore, the coupling methods may have very broad application prospect.
3. The innovative trimaleimide linkers provided by the invention incorporate three maleimide groups within their structures, and thus can conjugate with antibody's interchain cysteine and/or other amino acid residues simultaneously by simple chemical method. Compared to ADC products obtained via traditional conjugation methods, the conjugates via the trimaleimide linkers have DAR~3 fraction as the main components (90%+) and much narrowed DAR distribution. As a result, the homogeneity of the products is greatly improved.

The present invention is further elaborated by examples. It should be understood that these examples are used to illustrate the present invention, while not limit its scope. The unstated experiment conditions are generally according to routine conditions or conditions suggested by manufacturers. Unless otherwise stated, all reactions were conducted under the protection of nitrogen (except for hydrogenation reaction), which was not repeatedly described in example.

Unless otherwise defined, all professional and scientific terms used in the present invention have the same meaning as those familiar by the expertise in the art. Furthermore, any method or material similar or equal to those used in the present invention can be applied herein. The optimized methods and materials used in the present invention are only used for illustration while not for limitation.

The general procedures used in the present invention are described below.

General Procedure A

Preparation of Antibody-Drug Conjugate

Tris(2-carboxyethyl)phosphine (TCEP, 10 eq, stock solution 10 mM) was added to a solution of antibody (2-10 mg/mL, containing 25 mM boric acid-sodium borate buffer, 25 mM NaCl and 1 mM diethylene triamine pentacetic acid (DTPA), pH 7.0-8.0). The reaction mixture was incubated at 37° C. in a shaker for 1 h, and then cooled to ~10° C. The reaction mixture was buffer-exchanged via ultrafiltration into a PBS buffer (100 mM $KH_2PO_4$—$K_2HPO_4$, 100 mM NaCl, 1 mM DTPA, pH 7.0-8.0). To the above solution cooled at 10° C. was added DMSO and 5-100 equivalent trimaleimide linker-(linker)-drug (stock solution in DMSO), and the volume percent of DMSO was controlled at ~15%. The conjugation reaction was incubated at 10° C. for 0.5 h.

Excess cysteine solution was added to the reaction mixture to quench the unreacted trimaleimide linker-(linker)-drug. The quenching reaction was kept at 10° C. for 30 min. The reaction mixture was ultrafiltered to remove excess cysteine and trimaleimide linker-(linker)-drug-cysteine adducts. The residual solution was sterile filtered through 0.2 μm filter, and kept at 4° C.

General Procedure B

SDS-PAGE Analysis

SDS-PAGE was measured using NuPAGE, 4-12%, Bis-Tris Gel on XCell SureLock® Mini-Cell protein electrophoresis instrument. A sample (≥10 μg by weight) was combined with the corresponding sampling buffer, and the mixture was heated at 70° C. water bath for 10 min. The sample and standard protein (5 μL/hole) were added to the spacer gel comb holes sequentially, and the electrophoresis was conducted at 220 V for 50 min. The gel was rinsed by deionized water, and stained in coomassie light blue G250 solution on a shaker for 16 h. The stained gel was rinsed by deionized water for three times, and destained on a shaker for 4 h. The destained gel was transferred to an imager to record the gel image.

General Procedure C

Hydrophobic Interaction Chromatography (HIC) Analysis

HIC was measured on an Agilent 1100 chromatographic instrument. TSKgel butyl-NPR column (4.6×35 mm, 2.5

μm, Tosoh Bioscience Shanghai Co. Ltd.) was applied as the stationary phase. The method consisted of a linear gradient from 100% buffer A (50 mM potassium phosphate (pH 7.0)+1.5 M ammonium sulfate) to 100% buffer B (80% v/v 50 mM sodium phosphate (pH 7.0), 20% v/v isopropanol) in 25 minutes. The flow rate was 0.8 mL/min, the column temperature was 30° C., and the detection wavelengths were 230 and 280 nm.

General Procedure D
Size Exclusion Chromatography (SEC) Analysis

SEC was measured on an Agilent 1100 chromatographic instrument. TSKgel G3000SWXL column (7.8×300 mm, 5 μm, Tosoh Bioscience Shanghai Co. Ltd.) was applied as the stationary phase. The eluting solution was 100 mM sodium sulfate/100 mM sodium phosphate, pH 6.6 (containing 0.05% sodium azide). The flow rate was 1.0 mL/min, the column temperature was 25° C., and the detection wavelength was 280 nm.

General Procedure E
Determination of Average DAR

The average DAR for the ADC product was measured by UV absorption method (Clin. Cancer Res. 2004, 10, 7063-7070; WO 2011/039721).

$$DAR=(\varepsilon_{Ab248}-R*\varepsilon_{Ab280})/(R*\varepsilon_{D280}-\varepsilon_{D248})$$

wherein, $\varepsilon_{Ab248}$ and $\varepsilon_{Ab280}$ are molar extinction coefficients for the antibody at 248 nm and 280 nm, respectively. $\varepsilon_{D280}$ and $\varepsilon_{D248}$ are molar extinction coefficients for vcMMAE at 248 nm and 280 nm, respectively. $R=A_{248}/A_{280}$, wherein $A_{248}$ and $A_{280}$ are the absorbances of the ADC at 248 nm and 280 nm, respectively (peak area of the monomer on SEC spectrum was used to represent the absorbance in the invention).

General Procedure F
Native Mass Analysis

1 μL of PNGase F (New England Biolabs, USA) was added to 50 mg of ADC sample, and the reaction mixture was incubated at 37° C. for 2 h. The deglycosylated ADC sample was buffer-exchanged into ammonium acetate buffer (10 mM, pH 7.5), and the buffer exchange procedure was repeated for 10 times. The concentration was adjusted to 5 μM and directly injected into the high-resolution mass spectrometer (Orbitrap Exactive Plus EMR, Germany; the ion source is NanoFlex Source with emitter, NewObjective, USA). The mass data was collected under the positive ion mode, and the native mass data was analyzed by Protein Deconvolution 3.0 software (Thermo Fisher Scientific, Germany).

General Procedure G
Enzyme-Linked Immunosorbent Assay (ELISA)

Indirect ELISA was used to analyze binding ability of the antibody or antibody-drug conjugate to the corresponding antigen. The Her2 antigen was immobilized on a solid-phase support (96 well microplate) by coating to form a solid-phase antigen, and then unbound antigen was removed by washing. Serial dilutions of test antibody or antibody-drug conjugate were added, wherein specific antibody or antibody-drug conjugate bound to the antigen and formed solid-phase antigen-antibody complexes. The antibody or antibody-drug conjugate unbound to the solid-phase antigen was removed by washing. The enzyme labeled anti-antibody was added to bind to the above-formed complexes. After washing, substrate solution was added to develop color, and the optical density was read by a microplate reader at 450 nm/630 nm, based on which the $EC_{50}$ was calculated.

General Procedure H
Cell Proliferation Assay

Generally, the cytotoxic or cytostatic activity of an antibody-drug conjugate is measured by the following: exposing mammalian cells having tumor-associated antigens or receptor proteins to the antibody or the ADC in a cell culture medium; culturing the cells for a period from about 2 to 5 days; and measuring cell viability, based on which the curve was drawn and the $IC_{50}$ was calculated.

Unless otherwise stated, all anhydrous solvents were purchased from the suppliers and kept under nitrogen. All other reagents and solvents were purchased at high purity and not purified before use.

$^1$H NMR spectrum was collected on a Bruker Avance III 500 MHz instrument. Chemical shift (δ) unit is ppm, and the reference reagent is TMS (δ=0). The coupling constant (J) unit is Hz.

For LC-MS, low resolution mass spectrum was collected on Agilent 6110 (acid method) or 6120B (base method) mass spectrometers coupled with Hewlette-Packard Agilent 1200 HPLC.

Method 1: Waters Sunfire C18 reverse phase column (4.60×50 mm, 3.5 μm) was used in the acid HPLC method for separation, and the eluting gradient was 5%-95% B (acetonitrile, containing 0.01% TFA) in A (water, containing 0.01% TFA) in 1.4 min. The flow rate was 2.3 mL/min, and the column temperature was 50° C.

Method 2: Waters) (bridge C18 reverse phase column (4.60×50 mm, 3.5 μm) was used in the base HPLC method for separation, and the eluting gradient was 5%-95% B (acetonitrile) in A (water, containing 10 mM ammonium bicarbonate) in 1.5 min. The flow rate was 2.0 mL/min, and the column temperature was 40° C.

Purification by preparative HPLC was conducted on a Gilson instrument. Waters Sunfire C18 reverse phase column (250×19 mm, 10 μm) was used for separation.

Method 3: The acid HPLC preparation method. Mobile phase: A was aqueous solution containing 0.1% TFA; B was acetonitrile (ACN). The flow rate was 20 mL/min.

Method 4: The base HPLC preparation method. Mobile phase: A was aqueous solution containing 10 mM ammonium bicarbonate; B was acetonitrile (ACN). The flow rate was 20 mL/min.

SK-BR-3 human breast cancer cell was purchased from ATCC. Her2 antigen was purchased from Sino Biological Inc (Beijing) Antibody H (Herceptin Biosimilar, IgG1) was purchased from Genor Biopharma Co. Ltd. (Shanghai). The enzyme labeled anti-antibody was purchased from Sigma (Shanghai). Substrate solution was purchased from Decent Biotech (Shanghai). Cell Counting Kit (CCK-8) cell proliferation and cytotoxicity assay kit was purchased from Dojindo (Shanghai).

EXAMPLE 1

Preparation of Compound 1

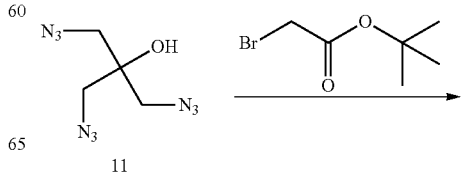

-continued

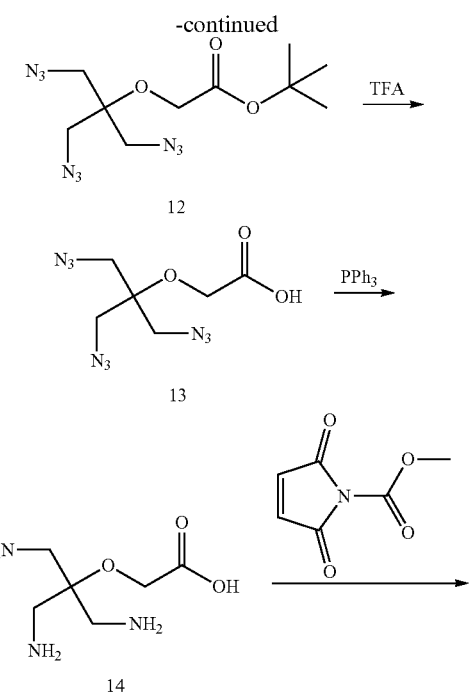

acetonitrile, and the suspension was filtered to give a white solid 14 (1.0 g). $^1$H NMR (500 MHz, D$_2$O) δ3.49 (s, 2H), 3.38 (d, 2H), 3.23 (d, 2H).

Step 4

Saturated sodium bicarbonate solution (20 mL) and THF (20 mL) were added to compound 14 (1.0 g, 3.5 mmol), and the solution was cooled to 0° C. N-methoxycarbonylmaleimide (1.95 g, 12.6 mmol) was added in batches, and the reaction mixture was stirred at 0° C. for 10 min, and then stirred at rt for 3 h. HCl solution was added to adjust pH to 2~3, and the product was extracted with EtOAc (50 mL×3). The combined organic phase was washed with brine, dried and concentrated. The residue was purified by prep-RP-HPLC (Method 3: 10%-35% B in 8 min to 95% B in 4 min) to give a white solid 1 (17 mg). LC-MS (Method 1): R$_t$=1.45 min; m/z (ES$^+$) 418.1 (M+H)$^+$. $^1$H NMR (500 MHz, DMSO-d$_6$) δ7.05 (s, 6H), 4.19 (s, 2H), 3.64 (s, 6H).

EXAMPLE 2

Preparation of Compound 2

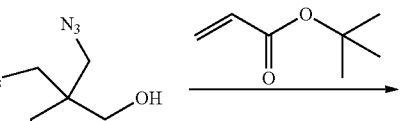

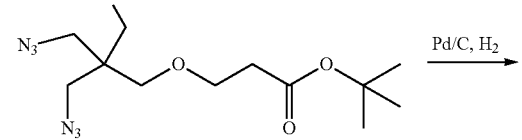

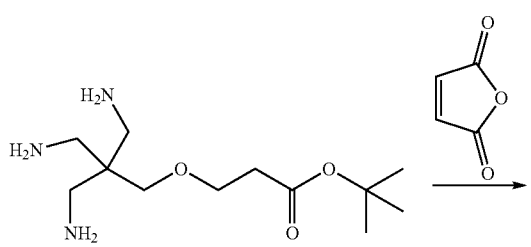

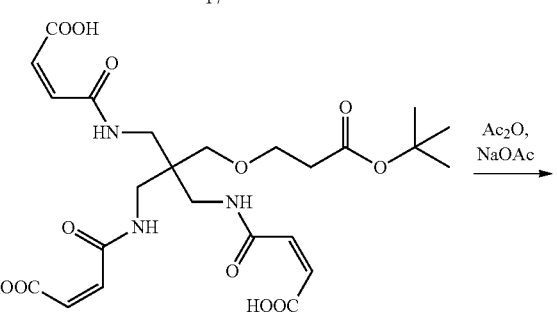

Step 1

Compound 11 (1.4 g, 7.1 mmol, preparation reference: U.S. Pat. No. 6,841,690) and tert-butyl bromoacetate (2.86 mL, 17.8 mmol) were dissolved in anhydrous THF (5 mL), and sodium hydride (60% dispersion in mineral oil, 1.28 g, 32.0 mmol) was added slowly within 1 h. The reaction mixture was stirred at rt for 1 h, and filtered through celite. The filtrate was concentrated, and the residue was purified by silica gel chromatography (PE/EtOAc 20:1 to 10:1) to give pale yellow oil 12 (2.0 g). $^1$H NMR (500 MHz, CDCl$_3$) δ4.13 (s, 2H), 3.51 (s, 6H), 1.49 (s, 9H).

Step 2

Compound 12 (1.4 g, 4.5 mmol) was dissolved in DCM (10 mL), to which TFA (5 mL) was added. The reaction mixture was stirred at rt for 3 h. The solvent was removed by concentration to give the crude 13 (1.3 g), which was used directly for next step.

Step 3

Compound 13 (1.3 g, 5.1 mmol) was dissolved in a mixed solution of THF (10 mL)/H$_2$O (1 mL), to which triphenylphosphine (4.8 g, 18.3 mmol) was added. The reaction mixture was stirred at rt overnight, and the solid was removed by filtration. The filtrate was diluted with water (20 mL) and extracted with diethyl ether. 2 M HCl (5 mL) was added to the aqueous phase, and then the solvent was removed by concentration. The residue was triturated with -continued

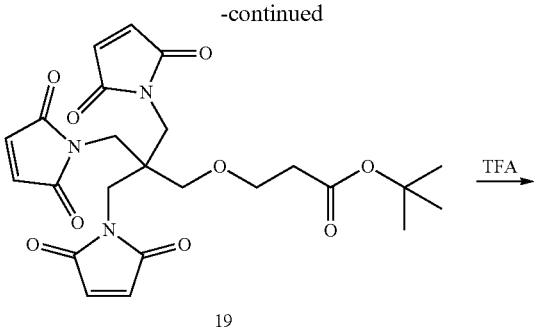

19

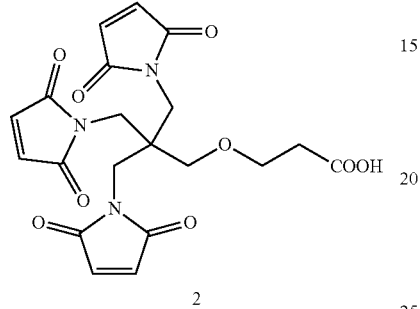

2

Step 1

Compound 15 (0.35 g, 1.55 mmol, preparation reference: Bioorganic and Medicinal Chemistry 1999, 7, 2303-2311) was dissolved in THF (5 mL), to which sodium hydride (60% dispersion in mineral oil, 6.6 mg, 0.17 mmol) and tert-butyl acrylate (480 μL, 3.31 mmol) were added sequentially. The reaction mixture was stirred at rt for 6 h, and the solvent was removed by concentration. The residue was purified by silica gel chromatography (PE/EtOAc 10:1) go give pale yellow oil 16 (0.45 g). LC-MS (Method 2): $R_t$=2.36 min; m/z (ES$^+$) 362.3 (M+Na)$^+$.

Step 2

Compound 16 (0.45 g, 1.33 mmol) was dissolved in ethanol, and then Pd/C (10%, 0.1 g) was added under a nitrogen atmosphere. The system was flushed with hydrogen for 3 times, and then the reaction mixture was stirred at rt under hydrogen for 8 h. The mixture was passed through a pad of celite, and the solid was washed with DCM. The filtrate was concentrated to give crude 17 (0.38 g), which was used directly for next step. LC-MS (Method 2): $R_t$=1.39 min; m/z (ES$^+$) 262.3 (M+H)$^+$.

Step 3

Compound 17 (0.38 g, 1.45 mmol) was dissolved in acetic acid (5 mL), to which maleic anhydride (0.71 g, 7.24 mmol) was added. The reaction mixture was stirred at rt for 16 h, and then concentrated under high vacuum to give crude 18, which was used directly for next step. LC-MS (Method 1): $R_t$=1.64 min; m/z (ES$^+$) 556.3 (M+H)$^{30}$.

Step 4

The crude 18 obtained in Step 3 was dissolved in acetic anhydride (15 mL), to which sodium acetate (48 mg, 0.58 mmol) was added. The reaction mixture was stirred at 100° C. for 1 h, and then poured onto crushed ice. The aqueous phase was extracted with ethyl acetate, and the organic phase was sequentially washed with saturated sodium bicarbonate and brine, dried, and concentrated. The residue was purified by silica gel chromatography (PE/EtOAc 2:1) to give the crude, which was further purified by prep-RP-HPLC (Method 3: 35%-55% B in 8 min→95% B in 4 min)

to give colorless oil 19 (30 mg). LC-MS (Method 1): $R_t$=1.86 min; m/z (ES$^+$) 524.2 (M+Na)$^{30}$.

Step 5

Compound 19 (30 mg, 0.06 mmol) was dissolved in DCM (3 mL), to which TFA (1 mL) was added. The reaction mixture was stirred at rt for 1 h, and the solvent was removed by concentration. Methanol was added to the residue, and the white precipitate was collected by filtration, washed, and dried to give a white solid 2 (12 mg). LC-MS (Method 1): $R_t$=1.51 min; m/z (ES$^+$) 446.1 (M+H)$^+$. $^1$H-NMR (500 MHz, DMSO-d$_6$) δ12.11 (s, 1H), 7.04 (s, 6H), 3.44 (s, 6H), 3.25 (t, 2H), 3.08 (s, 2H), 2.28 (t, 2H).

EXAMPLE 3

Preparation of Compound 3

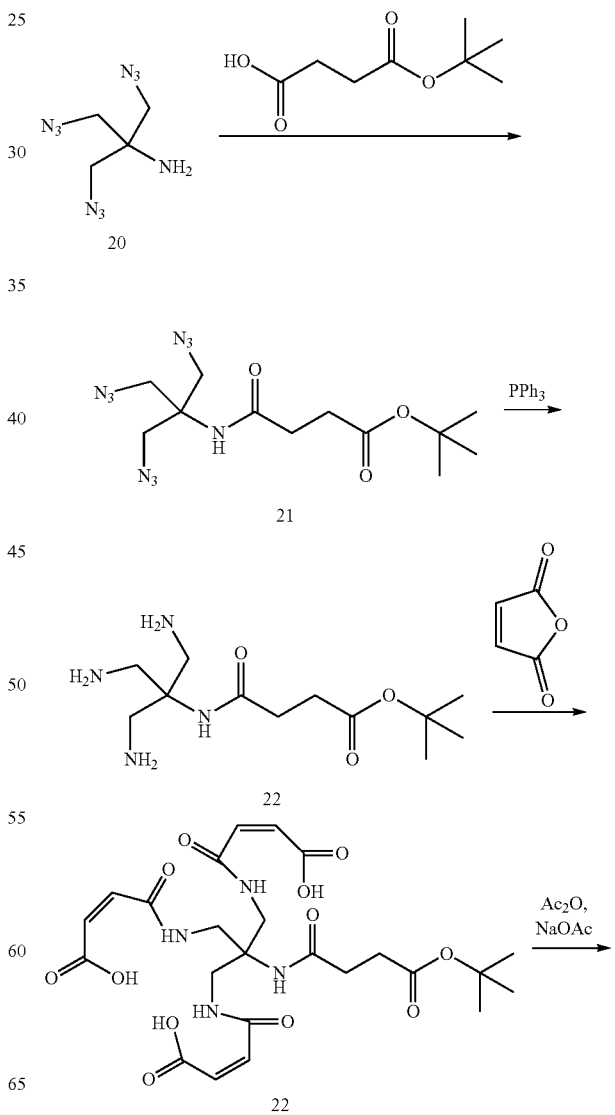

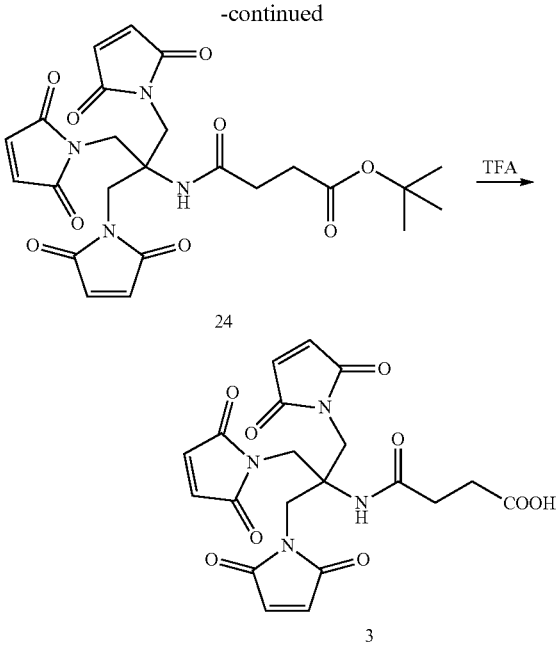

Step 1

Compound 20 (500 mg, 2.55 mmol, preparation reference: Journal of Polymer Science: Part A: Polymer Chemistry, 2004, 42, 4392-4403), mono-tert-butyl succinate (666 mg, 3.83 mmol) and HATU (1.94 g, 5.1 mmol) were dissolved in DCM (10 mL), to which DIEA (986 mg, 7.65 mmol) was added. The reaction mixture was stirred at rt for 4 h, and the solvent was removed by concentration. Ethyl acetate was added to the residue, and the organic phase was sequentially washed with water and brine, dried and concentrated. The crude product was purified by silica gel chromatography (PE/EtOAc 10:1) to give colorless oil 21 (810 mg). LC-MS (Method 2): $R_t$=2.14 min; m/z (ES$^+$) 297.1 (M+H)$^+$.

Step 2

Compound 21 (225 mg, 0.64 mmol) was dissolved in THF (10 mL), to which water (1 mL) and triphenylphosphine (1.0 g, 3.84 mmol) were added sequentially. The reaction mixture was stirred at rt overnight, and the solvent was removed by concentration. Water (10 mL) was added to the residue, and the solid was removed by filtration. The filtrate was concentrated to give a yellow solid 22 (160 mg), which was used directly for next step. LC-MS (Method 2): $R_t$=1.34 min; m/z (ES$^+$) 275.2 (M+H)$^+$.

Step 3

Compound 22 (153 mg, 0.56 mmol) was dissolved in acetic acid (5 mL), to which maleic anhydride (384 mg, 3.92 mmol) was added. The reaction mixture was stirred at rt for 2 d, and the solvent was removed by concentration. The crude was purified by prep-RP-HPLC (Method 3: 20%-45% B in 8 min→95% B in 4 min) to give a white solid 23 (60 mg). LC-MS (Method 1): $R_t$=1.26 min; m/z (ES$^+$) 569.2 (M+H)$^+$.

Step 4

Compound 23 (160 mg, 0.28 mmol) was dissolved in acetic anhydride (10 mL), to which sodium acetate (12 mg) was added. The reaction mixture was stirred at 100° C. for 4 h, and then the solvent was removed by concentration. Water (20 mL) was added to the residue, and then the aqueous phase was extracted with ethyl acetate (20 mL×3). The combined organic phase was washed with brine, dried, and concentrated. The crude product was purified by prep-RP-HPLC (Method 3: 35%-55% B in 9.5 min→95% B in 3 min) to give a brown solid 24 (20 mg). LC-MS (Method 1): $R_t$=1.42 min; m/z (ES$^+$) 515.2 (M+H)$^+$.

Step 5

Compound 24 (20 mg, 0.039 mmol) was dissolved in DCM (3 mL), to which TFA (89 mg, 0.78 mmol) was added. The reaction mixture was stirred at rt for 2 h, and then the solvent was removed by concentration. The residue was purified by prep-RP-HPLC (Method 3: 20%-37% B in 6.5 min→95% B in 5 min; Rt: min) to give a white solid 3 (5 mg). LC-MS (Method 1): $R_t$=1.44 min; m/z (ES$^+$) 459.1 (M+H)$^+$. $^1$H NMR (500 MHz, DMSO-d$_6$) δ12.02 (s, 1H), 7.38 (s, 1H), 7.05 (s, 6H), 3.78 (s, 6H), 2.43 (t, 2H), 2.24 (t, 2H).

EXAMPLE 4

Preparation of Compound 4

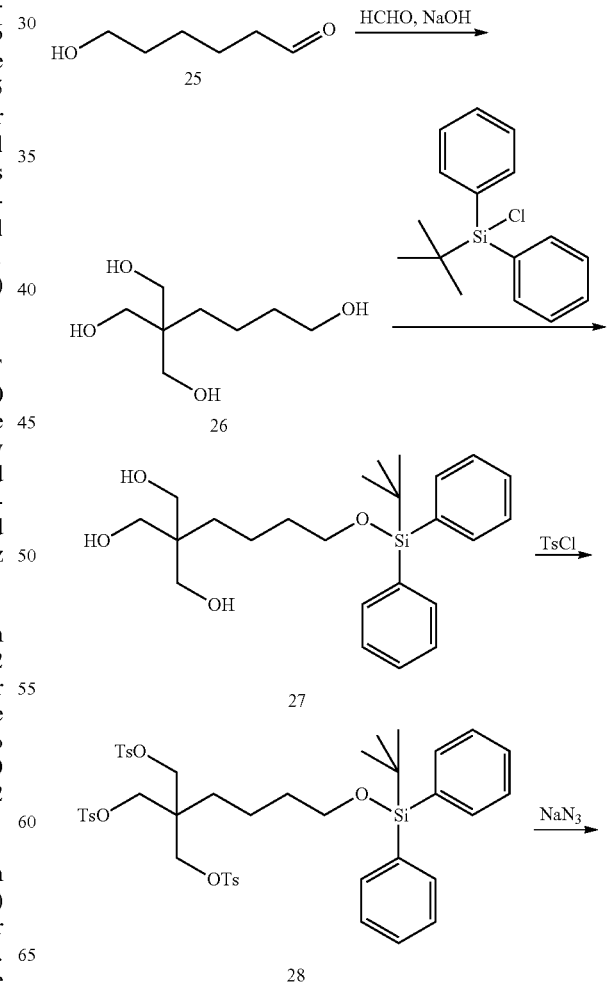

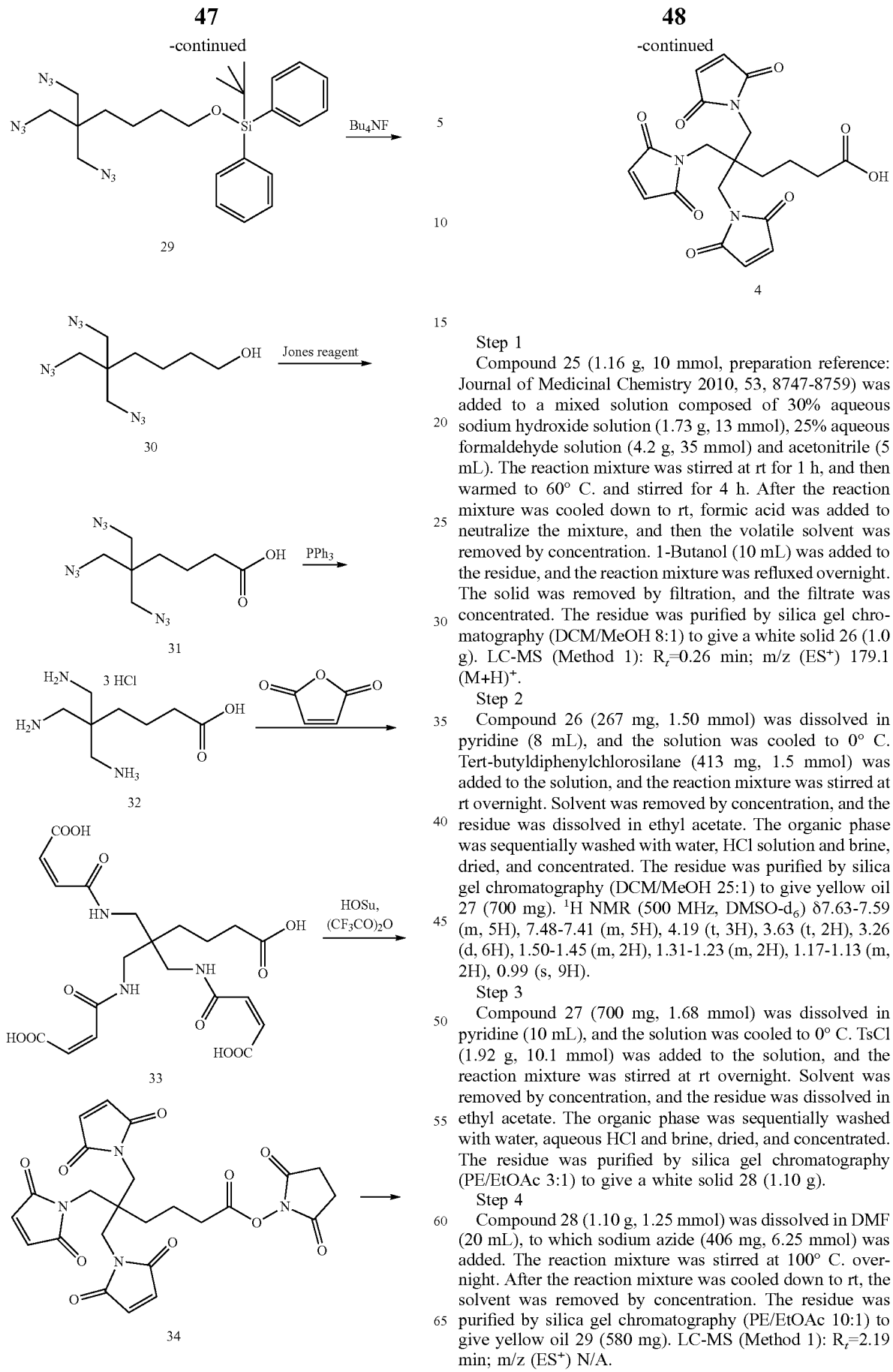

Step 1

Compound 25 (1.16 g, 10 mmol, preparation reference: Journal of Medicinal Chemistry 2010, 53, 8747-8759) was added to a mixed solution composed of 30% aqueous sodium hydroxide solution (1.73 g, 13 mmol), 25% aqueous formaldehyde solution (4.2 g, 35 mmol) and acetonitrile (5 mL). The reaction mixture was stirred at rt for 1 h, and then warmed to 60° C. and stirred for 4 h. After the reaction mixture was cooled down to rt, formic acid was added to neutralize the mixture, and then the volatile solvent was removed by concentration. 1-Butanol (10 mL) was added to the residue, and the reaction mixture was refluxed overnight. The solid was removed by filtration, and the filtrate was concentrated. The residue was purified by silica gel chromatography (DCM/MeOH 8:1) to give a white solid 26 (1.0 g). LC-MS (Method 1): $R_t$=0.26 min; m/z (ES$^+$) 179.1 (M+H)$^+$.

Step 2

Compound 26 (267 mg, 1.50 mmol) was dissolved in pyridine (8 mL), and the solution was cooled to 0° C. Tert-butyldiphenylchlorosilane (413 mg, 1.5 mmol) was added to the solution, and the reaction mixture was stirred at rt overnight. Solvent was removed by concentration, and the residue was dissolved in ethyl acetate. The organic phase was sequentially washed with water, HCl solution and brine, dried, and concentrated. The residue was purified by silica gel chromatography (DCM/MeOH 25:1) to give yellow oil 27 (700 mg). $^1$H NMR (500 MHz, DMSO-d$_6$) δ7.63-7.59 (m, 5H), 7.48-7.41 (m, 5H), 4.19 (t, 3H), 3.63 (t, 2H), 3.26 (d, 6H), 1.50-1.45 (m, 2H), 1.31-1.23 (m, 2H), 1.17-1.13 (m, 2H), 0.99 (s, 9H).

Step 3

Compound 27 (700 mg, 1.68 mmol) was dissolved in pyridine (10 mL), and the solution was cooled to 0° C. TsCl (1.92 g, 10.1 mmol) was added to the solution, and the reaction mixture was stirred at rt overnight. Solvent was removed by concentration, and the residue was dissolved in ethyl acetate. The organic phase was sequentially washed with water, aqueous HCl and brine, dried, and concentrated. The residue was purified by silica gel chromatography (PE/EtOAc 3:1) to give a white solid 28 (1.10 g).

Step 4

Compound 28 (1.10 g, 1.25 mmol) was dissolved in DMF (20 mL), to which sodium azide (406 mg, 6.25 mmol) was added. The reaction mixture was stirred at 100° C. overnight. After the reaction mixture was cooled down to rt, the solvent was removed by concentration. The residue was purified by silica gel chromatography (PE/EtOAc 10:1) to give yellow oil 29 (580 mg). LC-MS (Method 1): $R_t$=2.19 min; m/z (ES$^+$) N/A.

Step 5

Compound 29 (540 mg, 1.10 mmol) was dissolved in THF (10 mL), to which tetra(n-butyl)ammonium fluoride (1 M in THF, 1.65 mL, 1.65 mmol) was added. The reaction mixture was stirred at rt overnight. Water (20 mL) was added to the mixture, which was then extracted with ethyl acetate (20 mL×3). The combined organic phase was sequentially washed with brine, dried, and concentrated. The residue was purified by silica gel chromatography (PE/EtOAc 3:1) to give colorless oil 30 (222 mg). $^1$H NMR (500 MHz, DMSO-$d_6$) δ4.38 (t, 1H), 3.40-3.37 (m, 2H), 3.34 (s, 6H), 1.40-1.38 (m, 2H), 1.27-1.23 (m, 4H).

Step 6

Compound 30 (172 mg, 0.68 mmol) was dissolved in acetone (5 mL), and the solution was cooled to 0° C., to which Jone's reagent (0.38 mL, 1.02 mmol) was added. The reaction mixture was stirred at 0° C. for 1 h, and then quenched by addition of isopropanol until the solution color was green. The mixture was extracted by diethyl ether (50 mL×3), and the combined organic phase was sequentially washed with brine, dried and concentrated. The residue was purified by silica gel chromatography (PE/EtOAc 1:1) to give yellow oil 31 (150 mg). LC-MS (Method 1): $R_t$=1.50 min; m/z (ES$^+$) 290.1 (M+Na)$^+$. $^1$H NMR (500 MHz, CDCl$_3$) δ3.28 (s, 6H), 2.38 (t, 2H), 1.61-1.55 (m, 2H), 1.37-1.34 (m, 2H).

Step 7, 8

Compound 31 (100 mg, 0.37 mmol) was dissolved in THF (5 mL), to which triphenylphosphine (490 mg, 1.87 mmol) and water (34 μL, 1.87 mmol) were added sequentially. The reaction mixture was stirred at rt for 16 h, and then the solvent was removed by concentration. The residue was diluted by adding water (10 mL), and the aqueous phase was extracted with diethyl ether (10 mL×3). The aqueous phase was acidified by the addition of 2 mL of conc. HCl, and the solvent was removed by concentration. The residue was triturated with ethanol, and the solid was collected by filtration, washed, and dried to give a beige solid. The solid was dissolved in acetic acid (5 mL), to which maleic anhydride (183 mg, 1.87 mmol) and sodium acetate (153 mg, 1.87 mmol) were added. The reaction mixture was stirred at rt for 16 h, and the solvent was removed by concentration. The residue was purified by prep-RP-HPLC (Method 3: 5%-30% B in 8 min→95% B in 4 min) to give a white solid 33 (110 mg). LC-MS (Method 1): $R_t$=1.38 min; m/z (ES$^+$) 484.2 (M+H)$^+$. $^1$H NMR (500 MHz, DMSO-$d_6$) δ8.54 (t, 3H), 6.48 (d, 3H), 6.20 (d, 3H), 3.14 (d, 6H), 2.14 (t, 2H), 1.23-1.19 (m, 4H).

Step 9

Compound 33 (100 mg, 0.21 mmol) was dissolved in DMF (2 mL), and then the solution was cooled to 0° C., to which 2,4,6-trimethylpyridine (0.14 mL, 1.04 mmol) was added. The mixture was marked as mixture A. N-hydroxysuccinimide (0.95 g, 8.26 mmol) was dissolved in DMF (10 mL), and the solution was cooled to 0° C., to which trifluoroacetic anhydride (1.17 mL, 8.30 mmol) was added dropwise. The reaction mixture was stirred for 10 min, and then 2,4,6-trimethylpyridine (1.09 mL, 8.30 mmol) was added dropwise. After the reaction mixture was stirred for another 10 min, the mixture was added dropwise to mixture A within 0.5 h. Once the addition was completed, the reaction mixture was warmed to rt and stirred overnight. Water (30 mL) was added, and the mixture was extracted with EtOAc (20 mL×2). The combined organic phase was sequentially washed with water (20 mL×2), dried and concentrated. The residue was purified by prep-RP-HPLC (Method 3: 20%-50% B in 8 min→95% B in 4 min) to give a white solid 34 (50 mg). LC-MS (Method 1): $R_t$=1.70 min; m/z (ES$^+$) 527.2 (M+H)$^+$. $^1$H NMR (500 MHz, CDCl$_3$) δ6.75 (s, 6H), 3.61 (s, 6H), 2.81 (s, 4H), 2.51 (t, 2H), 1.96-1.93 (m, 2H), 1.36-1.33 (m, 2H).

Step 10

Compound 34 (6 mg, 0.011 mmol) was dissolved in THF (2 mL), to which saturated sodium bicarbonate (2 mL) was added. The reaction mixture was stirred at rt for 1 h, and then was acidified by HCl solution to pH 2~3. The aqueous phase was extracted with ethyl acetate (10 mL×2), and the combined organic phase was dried and concentrated. The residue was purified by prep-RP-HPLC (Method 3: 20%-50% B in 8 min→95% B in 4 min) to give compound 4. LC-MS (Method 1): $R_t$=1.61 min; m/z (ES$^+$) 430.2 (M+H)$^+$.

EXAMPLE 5

Preparation of Compound 5

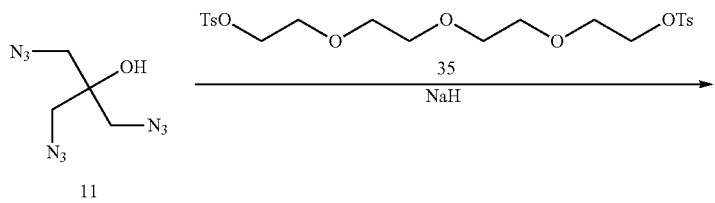

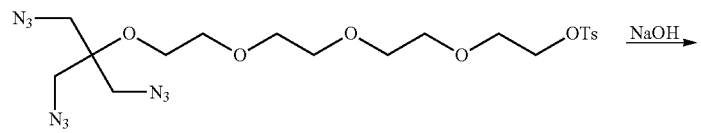

-continued
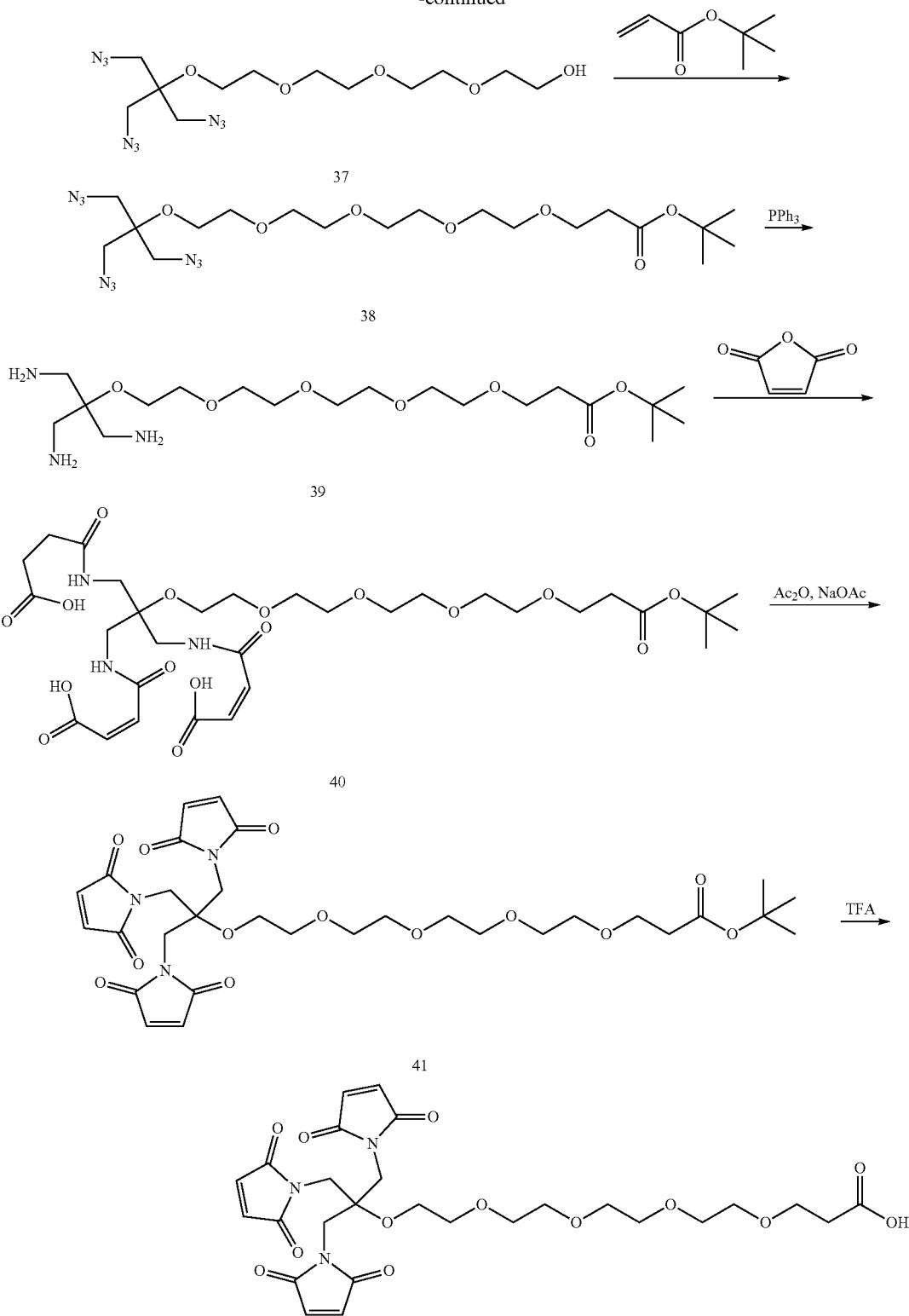
Step 1
Compound 11 (0.50 g, 2.54 mmol) was dissolved in anhydrous THF (5 mL), to which sodium hydride (60% dispersion in mineral oil, 122 mg, 3.05 mmol) was added. The reaction mixture was stirred at rt for 3 h, to which a solution of compound 35 (2.85 g, 5.67 mmol) in anhydrous THF (5 mL) was added, and the reaction mixture was refluxed for 16 h. The mixture was filtered through a pad of celite, and the solid was washed with DCM. The filtrate was concentrated to remove the solvent, and the residue was purified by silica gel chromatography (PE/EtOAc 3:1) to give colorless oil 36 (0.95 g). LC-MS (Method 2): $R_t$=2.19 min; m/z (ES$^+$) 545.3 (M+NH$_4$)$^+$.

Step 2

Compound 36 (0.95 g, 1.8 mmol) was dissolved in 1,4-dioxane (10 mL), to which aqueous sodium hydroxide (30%, 5 mL) was added. The reaction mixture was refluxed for 16 h. After the mixture was cooled down to rt, it was extracted with EtOAc (20 mL), and the organic phase was dried and concentrated. The residue was purified by silica gel chromatography (PE/EtOAc 1:1→1:2) to give pale yellow oil 37 (0.38 g). LC-MS (Method 2): $R_t$=1.84 min; m/z (ES$^+$) 391.3 (M+NH$_4$)$^+$.

Step 3

Compound 37 (0.38 g, 1.025 mmol) was dissolved in THF (5 mL), to which sodium hydride (60% dispersion in mineral oil, 4.0 mg, 0.1 mmol) and tert-butyl acrylate (296 μL, 2.04 mmol) were added sequentially. The reaction mixture was stirred at rt for 4 h, and then was concentrated to remove the solvent. The residue was purified by silica gel chromatography (PE/EtOAc 3:1) to give colorless oil 38 (0.13 g). LC-MS (Method 2): $R_t$=2.21 min; m/z (ES$^+$) 519.3 (M+NH$_4$)$^+$.

Step 4

Compound 38 (0.13 g, 0.26 mmol) was dissolved in THF (5 mL), to which water (23.4 μL, 1.3 mmol) and triphenylphosphine (0.34 g, 1.3 mmol) were added sequentially. The reaction mixture was stirred at rt for 8 h, and then was concentrated to remove the solvent. Water (10 mL) was added to the residue, and the mixture was washed with diethyl ether (5 mL×3). The aqueous phase was lyophilized to give colorless oil 39 (0.10 g), which was used directly for next step.

Step 5

Compound 39 (0.1 g, 0.24 mmol) was dissolved in acetic acid (3 mL), to which maleic anhydride (0.12 g, 1.18 mmol) was added. The reaction mixture was stirred at rt for 16 h, and then was concentrated to remove the solvent. The residue was purified by prep-RP-HPLC (Method 3: 20%-40% B in 8 min→95% B in 4 min) to give 40 (95 mg). LC-MS (Method 1): $R_t$=1.68 min; m/z (ES$^+$) 740.3 (M+Na)$^+$.

Step 6

Compound 40 (95 mg, 0.13 mmol) was dissolved in acetic anhydride (3 mL), to which sodium acetate (4.3 mg, 0.053 mmol) was added. The reaction mixture was stirred at 100° C. for 1.5 h, and then was poured onto crushed ice. The aqueous phase was extracted with ethyl acetate. The organic phase was sequentially washed with saturated sodium carbonate and brine, dried and concentrated. The residue was purified by silica gel chromatography (PE/EtOAc 1:1) to give colorless oil 41 (80 mg). LC-MS (Method 1): $R_t$=1.87 min; m/z (ES$^+$) 686.2 (M+Na)$^+$.

Step 7

Compound 41 (80 mg, 0.13 mmol) was dissolved in DCM (3 mL), to which TFA (1 mL) was added. The reaction mixture was stirred at rt for 3 h, and then was concentrated to remove the solvent. The residue was purified by prep-RP-HPLC (Method 3: 25%-45% B in 8 min→95% B in 4 min) to give a colorless stick solid 5 (30 mg). LC-MS (Method 1): $R_t$=1.55 min; m/z (ES$^+$) 608.2 (M+H)$^+$. $^1$H NMR (500 MHz, CDCl$_3$) δ6.75 (s, 6H), 3.81-3.77 (m, 10H), 3.65-3.58 (m, 12H), 3.45 (t, 2H), 2.62 (t, 2H).

EXAMPLE 6

Preparation of Compound 6

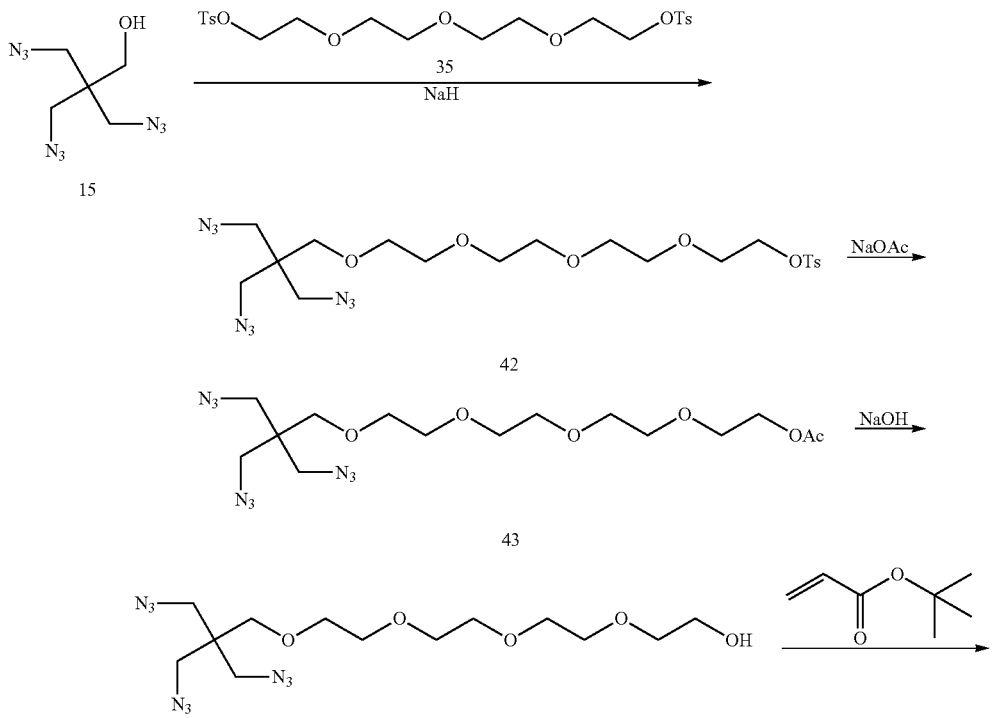

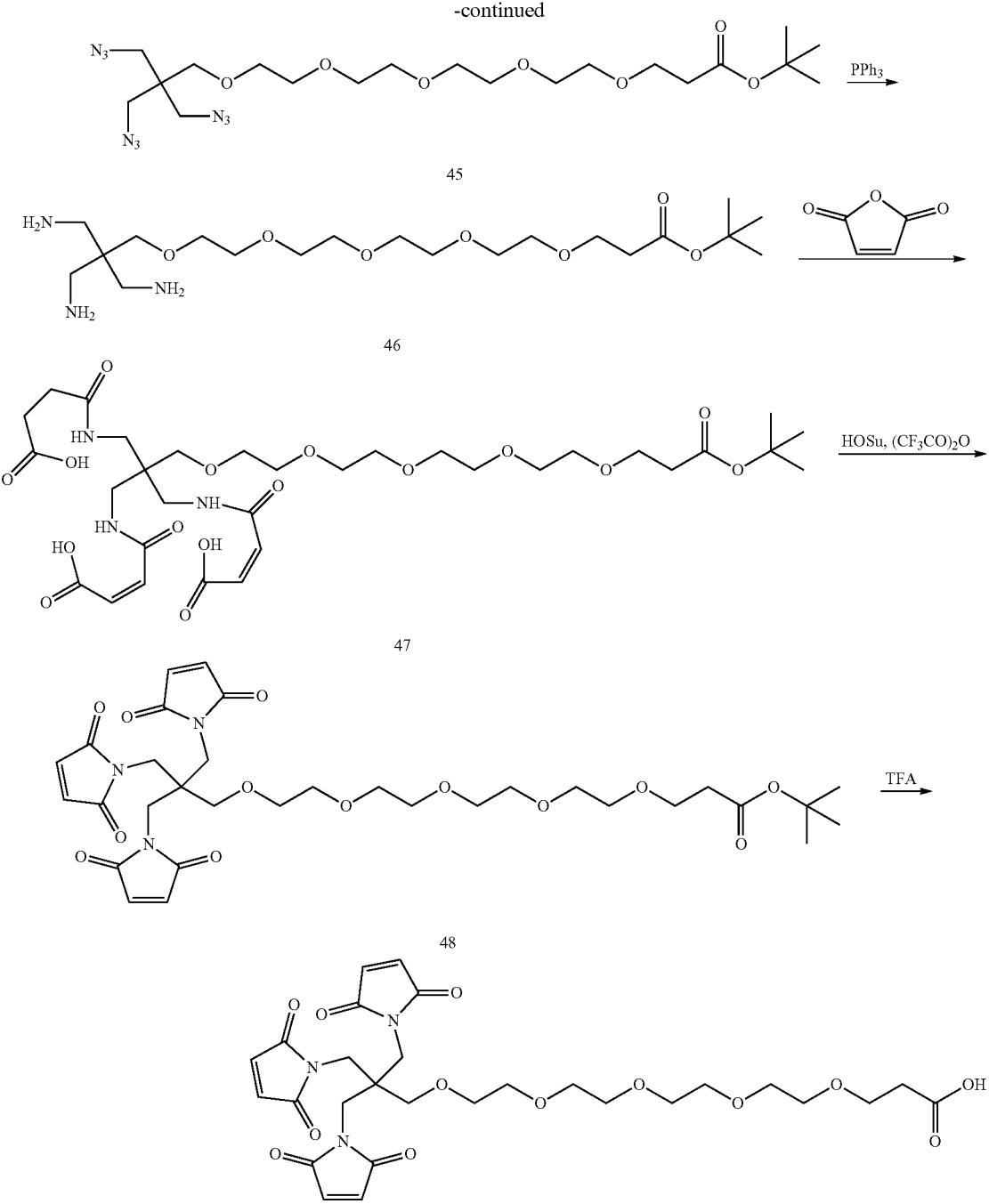

Step 1

Compound 15 (1.0 g, 4.74 mmol) was dissolved in anhydrous THF (10 mL), to which sodium hydride (60% dispersion in mineral oil, 380 mg, 9.5 mmol) was added. The reaction mixture was stirred at rt for 30 min, which was then added to a solution of 2,2'-(2,2'-oxybis(ethane-2,1-diyl)bis(oxy))bis(ethane-2,1-diyl)bis(4-methylbenzenesulfonate) (11.9 g, 23.7 mmol) in anhydrous THF (20 mL). The reaction mixture was refluxed for 16 h, and then was cooled to rt. The mixture was filtered through a pad of celite, and the filter cake was washed with DCM. The filtrate was concentrated, and the residue was purified by silica gel chromatography (PE/EtOAc 3:1) to give colorless oil 42 (8.0 g). LC-MS (Method 2): $R_t$=2.28 min; m/z (ES$^+$) 559.3 (M+NH$_4$)$^+$.

Step 2, 3

Compound 42 (2.20 g, 4.06 mmol) was dissolved in DMF (20 mL), to which sodium acetate (3.33 g, 40.6 mmol) was added. The reaction mixture was refluxed at 100° C. for 16 h, and then was concentrated to remove the solvent. The residue was dissolved in EtOAc (50 mL), and the mixture was filtered to remove the solid. The filtrate was sequentially washed with brine (20 mL×2), dried, and concentrated to give crude 43, which was used directly for next step. LC-MS (Method 2): $R_t$=2.11 min; m/z (ES$^+$) 447.3 (M+NH$_4$)$^+$. Crude 43 was dissolved in methanol (10 mL), to which 2.0 M sodium hydroxide (10 mL) was added. The reaction mixture was stirred at rt for 1 h, and then extracted with EtOAc. The organic phase was washed with brine, dried, and concentrated. The residue was purified by silica gel chromatography (PE/EtOAc 1:1→1:2) to give colorless oil 44 (1.26 g). LC-MS (Method 2): $R_t$=1.95 min; m/z (ES$^+$) 405.3 (M+NH$_4$)$^+$.

Step 4

Compound 44 (1.26 g, 3.25 mmol) was dissolved in THF (10 mL), to which sodium hydride (60% dispersion in mineral oil, 13 mg, 0.33 mmol) and tert-butyl acrylate (944 µL, 6.5 mmol) were added sequentially. The reaction mixture was stirred at rt for 16 h, and then was concentrated to remove the solvent. The residue was purified by silica gel chromatography (PE/EtOAc 3:1) to give colorless oil 45 (1.45 g). LC-MS (Method 2): $R_t$=2.31 min; m/z (ES$^+$) 533.3 (M+NH$_4$)$^+$. $^1$H NMR (500 MHz, CDCl$_3$) δ3.70 (t, 2H), 3.65-3.59 (m, 16H), 3.33 (m, 8H), 2.50 (t, 2H), 1.44 (s, 9H).

Step 5, 6

Compound 45 (200 mg, 0.39 mmol) was dissolved in THF (5 mL), to which triphenylphosphine (509 mg, 1.94 mmol) and water (35 µL, 1.94 mmol) were added sequentially. The reaction mixture was stirred at rt for 16 h, and then was concentrated to remove the solvent. Water (10 mL) was added to the residue, and then the mixture was extracted with diethyl ether (10 mL×3). The aqueous phase was lyophilized to give colorless oil. The oil was dissolved in acetic acid (5 mL), to which maleic anhydride (190 mg, 1.94 mmol) was added. The reaction mixture was stirred at rt for 16 h, and then was concentrated to remove the solvent. The residue was purified by prep-RP-HPLC (Method 3: 20%-40% B in 8 min→95% B in 4 min) to give colorless oil 47 (140 mg). LC-MS (Method 1): $R_t$=1.95 min; m/z (ES$^+$) 700.3 (M+H)$^+$. $^1$H NMR (500 MHz, CDCl$_3$) δ8.59 (s, 3H), 6.47 (d, 3H), 6.36 (d, 3H), 3.71-3.59 (m, 18H), 3.36-3.35 (m, 8H), 2.50 (t, 2H), 1.44 (s, 9H).

Step 7

Compound 47 (140 mg, 0.19 mmol) was dissolved in DMF (2 mL), and then the solution was cooled to 0° C., to which 2,4,6-trimethylpyridine (0.13 mL, 0.96 mmol) was added. The mixture was marked as solution A. N-hydroxysuccinimide (0.88 g, 7.65 mmol) was dissolved in DMF (10 mL), and then the mixture was cooled to 0° C., to which trifluoroacetic anhydride (1.08 mL, 7.65 mmol) was added dropwise. The reaction mixture was stirred for 10 min, and then 2,4,6-trimethylpyridine (1.01 mL, 7.65 mmol) was added dropwise. The reaction mixture was stirred for another 10 min, and then the mixture was dropwise added to solution A within 0.5 h. After the addition was completed, the reaction mixture was warmed to rt and stirred overnight. The mixture was diluted with water (30 mL), and then extracted with EtOAc (20 mL×2). The combined organic phase was sequentially washed with water (20 mL×2), dried, and concentrated. The residue was purified by prep-RP-HPLC (Method 3: 40%-60% B in 8 min→95% B in 4 min) to give a white solid 48 (77 mg). LC-MS (Method 1): $R_t$=1.70 min; m/z (ES$^+$) 527.2 (M+H)$^+$. $^1$H NMR (500 MHz, CDCl$_3$) δ6.72 (s, 6H), 3.68 (t, 2H), 3.62-3.54 (m, 18H), 3.47 (t, 2H), 3.29 (t, 2H), 3.18 (s, 2H), 2.48 (t, 2H), 1.42 (s, 9H).

Step 8

Compound 48 (77 mg, 0.11 mmol) was dissolved in DCM (6 mL), to which TFA (2 mL) was added. The reaction mixture was stirred at rt for 2 h, and then was concentrated to remove the solvent. The residue was purified by prep-RP-HPLC (Method 3: 20%-50% B in 8 min→95% B in 4 min) to give a colorless gum 6 (50 mg). LC-MS (Method 1): $R_t$=1.66 min; m/z (ES$^+$) 622.2 (M+H)$^+$. $^1$H NMR (500 MHz, CDCl$_3$) δ6.73 (s, 6H), 3.74 (t, 2H), 3.62-3.55 (m, 18H), 3.50 (t, 2H), 3.29 (t, 2H), 3.18 (s, 2H), 2.60 (t, 2H).

EXAMPLE 7

Preparation of Compound 7

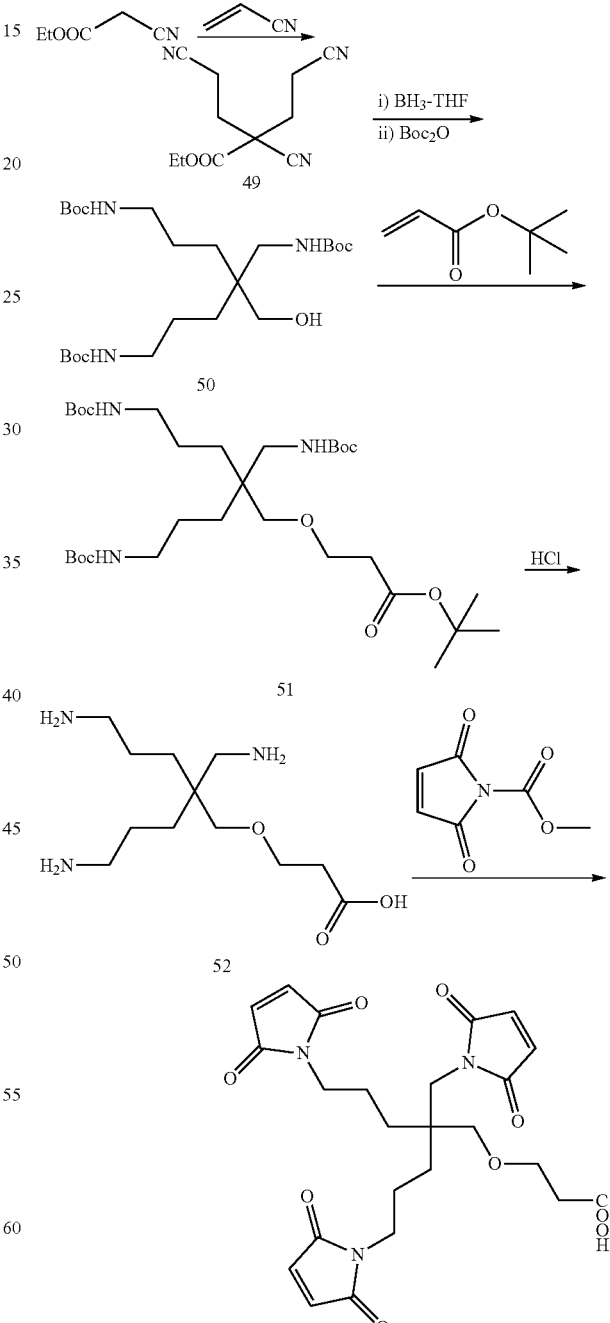

Step 1

Ethyl cyanoacetate (1.1 g, 9.7 mmol) and trimethylphenylammonium hydroxide (40% aq, 0.1 mL) were combined in 1,2-dimethoxyethane (5 mL), to which acrylonitrile (1.03 g, 19.4 mmol) was added dropwise within 30 min. The reaction mixture was stirred at rt for 16 h, and then was concentrated to remove the solvent. The residue was dissolved in DCM (30 mL), and the solution was washed sequentially with diluted HCl (0.5 N, 10 mL) and brine (15 mL), dried and concentrated. The residue was purified by silica gel chromatography (PE/EtOAc 4:1) to give colorless oil 49 (2.18 g). $^1$H NMR (500 MHz, CDCl$_3$) δ4.38 (q, 2H), 2.69-2.63 (m, 2H), 2.57-2.50 (m, 2H), 2.44-2.38 (m, 2H), 2.22-2.16 (m, 2H), 1.39 (t, 3H).

Step 2

Compound 49 (0.22 g, 1.0 mmol) was dissolved in anhydrous THF (5 mL), to which borane-tetrahydrofuran complex (1.0 M in THF, 10 mL, 10.0 mmol) was added. The reaction mixture was refluxed for 16 h, and then cooled down to rt. MeOH (3 mL) was added to quench the reaction, and then di-tert-butyl dicarbonate (1.1 g, 5 mmol) and TEA (0.7 mL, 5 mmol) were added. The reaction mixture was refluxed for 6 h, and then was concentrated to remove the solvent. The residue was dissolved in EtOAc (30 mL), and the organic phase was washed sequentially with diluted HCl (0.5 N) and brine, dried, and concentrated. The residue was purified by silica gel chromatography (PE/EtOAc 3:1→1:1) to give colorless oil 50 (0.15 g). LC-MS (Method 2): R$_t$=2.13 min; m/z (ES$^+$) 512.4 (M+Na)$^+$.

Step 3

Compound 50 (0.15 g, 0.31 mmol) was dissolved in THF (5 mL), to which sodium hydride (60% dispersion in mineral oil, 2.4 mg, 0.06 mmol) and tert-butyl acrylate (89 μL, 0.61 mmol) were sequentially added. The reaction mixture was stirred at rt for 16 h, and then was concentrated to remove the solvent. The residue was purified by silica gel chromatography (PE/EtOAC 5:1→3:1) to give colorless oil 51 (0.12 g). $^1$H NMR (500 MHz, DMSO-d$_6$) δ6.64 (t, 2H), 6.42 (t, 1H), 3.51 (t, 2H), 3.05 (s, 2H), 2.90-2.78 (m, 6H), 2.41 (t, 2H), 1.45-1.20 (m, 40H), 1.15-1.00 (m, 4H).

Step 4

Compound 51 (115 mg, 0.19 mmol) was dissolved in 1,4-dioxane (4 mL), to which conc. HCl (2 mL) was added. The reaction mixture was stirred at rt for 16 h, and then was concentrated to remove the solvent. Acetonitrile (20 mL) was added to the residue, and the mixture was concentrated again to give crude 52, which was used directly for next step.

Step 5

Saturated sodium bicarbonate (2.5 mL) and THF (2.5 mL) were added to the crude 52 obtained from last step, and the mixture was cooled to 0° C., to which N-(methoxycarbonyl) maleimide (144 mg, 0.93 mmol) was added in batches. The reaction mixture was stirred at 0° C. for 10 min, and then warmed to rt and stirred for 3 h. Diluted HCl was added to the mixed solution to adjust its pH to 2~3, and then the mixture was extracted with EtOAc (20 mL×2). The combined organic phase was dried and concentrated. The residue was purified by prep-RP-HPLC (Method 3: 20%-50% B in 8 min→95% B in 4 min) to give 7 (10 mg). LC-MS (Method 1): R$_t$=1.33 min; m/z (ES$^+$) 502.1 (M+H)$^+$. $^1$H NMR (500 MHz, DMSO-d$_6$) δ6.98 (s, 4H), 6.96 (s, 2H), 3.35-3.25 (m, 6H), 3.21 (s, 2H), 3.04 (s, 2H), 1.45-1.39 (m, 4H), 1.11-1.00 (m, 4H).

EXAMPLE 8

Preparation of Compound 8

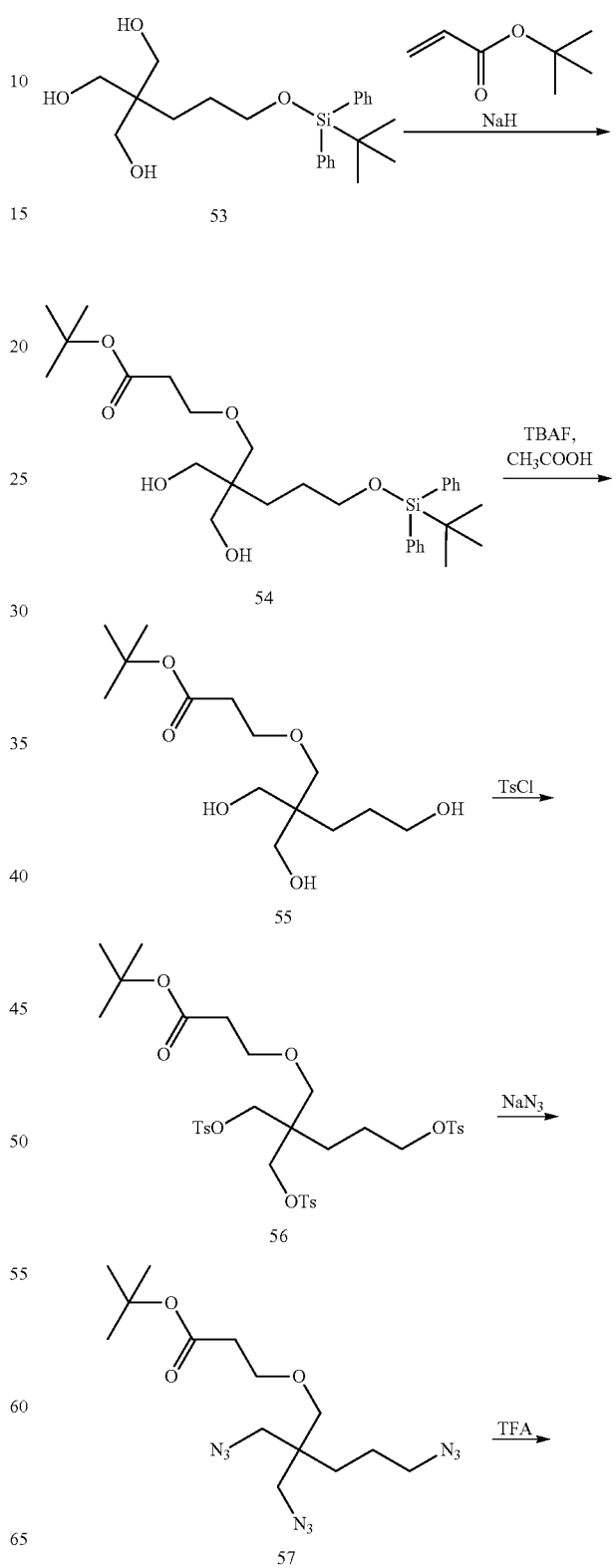

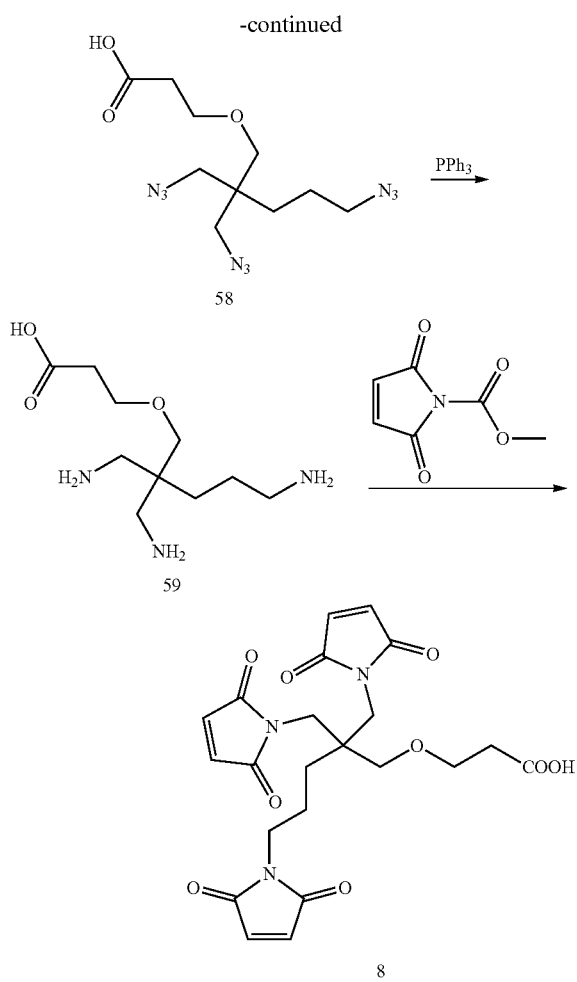

Step 1

Compound 53 (1.40 g, 3.48 mmol, preparation reference: US 2006/0189603) was dissolved in THF (5 mL), to which sodium hydride (60% dispersion in mineral oil, 7.0 mg, 0.17 mmol) and tert-butylacrylate (202 μL, 1.39 mmol) were sequentially added. The reaction mixture was stirred at rt for 16 h, and then was concentrated to remove the solvent. The residue was purified by silica gel chromatography (DCM/MeOH 50:1→20:1) to give colorless oil 54 (0.48 g). LC-MS (Method 2): $R_t$=2.56 min; m/z (ES$^+$) 553.3 (M+Na)$^+$.

Step 2

Compound 54 (0.48 g, 0.90 mmol) and acetic acid (78 μL, 1.36 mmol) were combined in THF (10 mL), and the mixture was cooled to 0° C., to which tetra(n-butyl)ammonium fluoride (1.0 M in THF, 1.36 mL, 1.36 mmol) was added. The reaction mixture was stirred at rt for 16 h, and then the solvent was removed by concentration. The residue was purified by silica gel chromatography (DCM/MeOH 10:1) to give colorless oil 55 (0.20 g). LC-MS (Method 2): $R_t$=1.60 min; m/z (ES$^+$) 315.3 (M+Na)$^+$.

Step 3

Compound 55 (0.20 g, 0.69 mmol) was dissolved in pyridine (5 mL). The solution was cooled to 0° C., to which TsCl (0.65 g, 3.42 mmol) was added. The reaction mixture was stirred at rt for 18 h, and then was concentrated to remove the solvent. The residue was purified by silica gel chromatography (PE/EtOAC 3:1) to give colorless oil 56 (0.17 g). LC-MS (Method 2): $R_t$=2.43 min; m/z (ES$^+$) 772.2 (M+Na)$^+$.

Step 4

Compound 56 (0.17 g, 0.23 mmol) was dissolved in DMF (5 mL), to which sodium azide (73 mg, 1.13 mmol) was added. The reaction mixture was stirred at 100° C. for 24 h, and then was concentrated to remove the solvent. The residue was purified by silica gel chromatography (PE/EtOAc 10:1) to give colorless oil 57 (57 mg). $^1$H NMR (500 MHz, CDCl$_3$) δ3.65 (t, 2H), 3.28-3.25 (m, 8H), 2.47 (t, 2H), 1.60-1.50 (m, 2H), 1.46 (s, 9H), 1.40-1.35 (m, 2H).

Step 5

Compound 57 (57 mg, 0.16 mmol) was dissolved in DCM (3 mL), to which TFA (1 mL) was added. The reaction mixture was stirred at rt for 3 h, and then was concentrated to remove the solvent. The residue was purified by silica gel chromatography (PE/EtOAc 3:1) to give compound 58 (41 mg). LC-MS (Method 2): $R_t$=1.61 min; m/z (ES$^+$) 310.2 (M−H)$^+$.

Step 6, 7

Compound 58 (41 mg, 0.13 mmol) was dissolved in THF (5 mL), to which triphenylphosphine (173 mg, 0.66 mmol) was added. The reaction mixture was stirred at rt for 16 h, and water (10 mL) was added. The mixture was extracted with diethyl ether (10 mL×3). The aqueous phase was lyophilized, and the residue was dissolved in a mixed solvent of saturated sodium bicarbonate (2.5 mL) and THF (2.5 mL). The mixture was cooled to 0° C., to which N-(methoxycarbonyl)maleimide (102 mg, 0.66 mmol) was added in batches. The reaction mixture was stirred at 0° C. for 10 min, and then stirred at rt for 3 h. The mixture was acidified with diluted HCl to pH 2~3, and then extracted with EtOAc (20 mL×2). The combined organic phase was dried and concentrated. The residue was purified by prep-RP-HPLC (Method 3: 20%-40% B in 8 min→95% B in 4 min) to give compound 8 (3 mg). LC-MS (Method 1): $R_t$=1.27 min; m/z (ES$^+$) 474.2 (M+H)$^+$. $^1$H NMR (500 MHz, DMSO-d$_6$) δ12.11 (br s, 1H), 7.02 (s, 4H), 6.99 (s, 2H), 3.37-3.21 (m, 8H), 3.13 (s, 2H), 2.32 (t, 2H), 1.57-1.51 (m, 2H), 1.16-1.13 (m, 2H).

EXAMPLE 9

Preparation of Compound 9

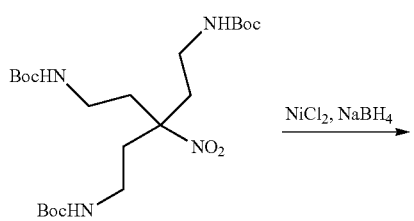

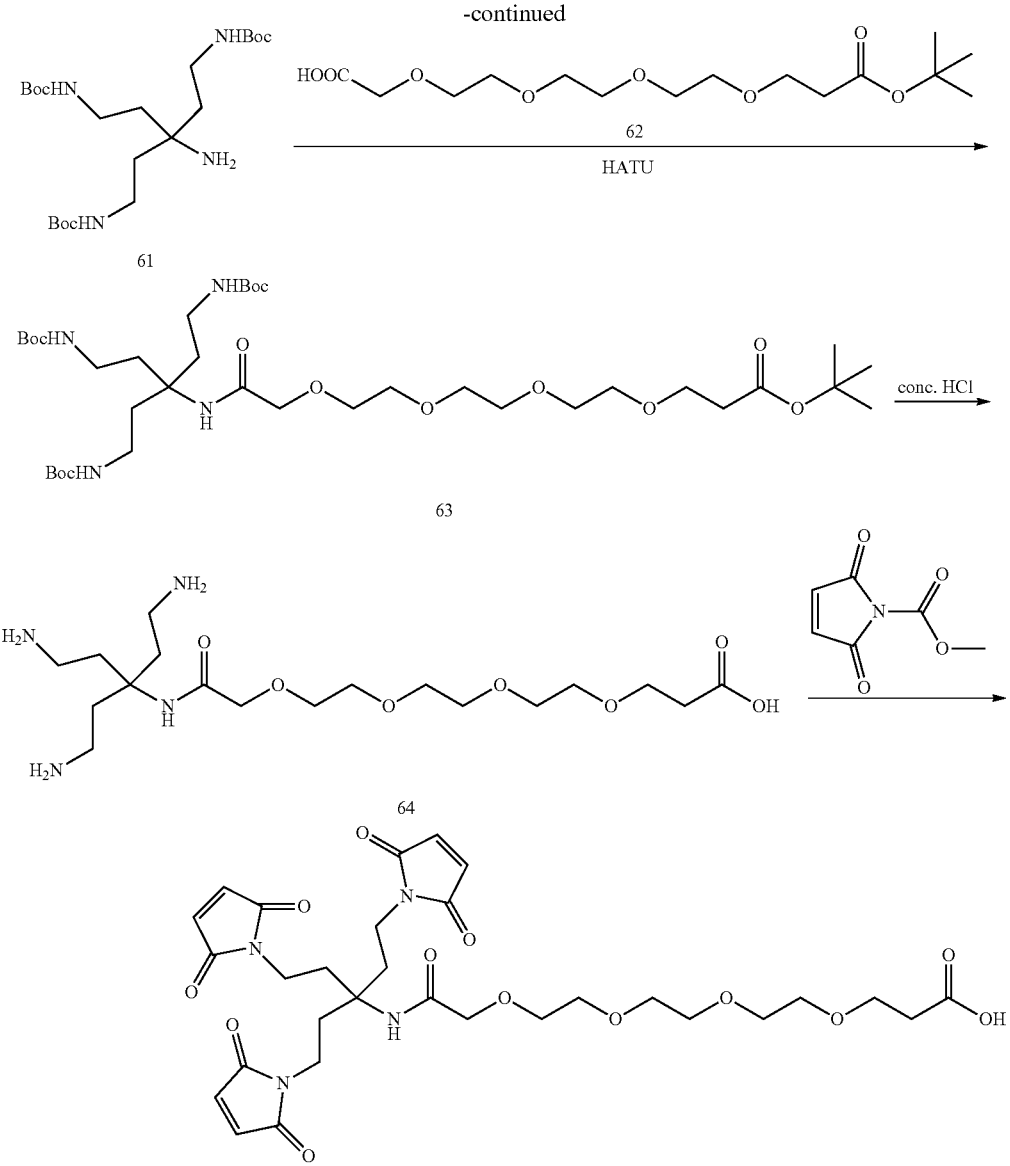

Step 1

Nnickel chloride (317 mg, 2.45 mmol) was dissolved in MeOH (30 mL) placed in a supersonic bath, to which sodium borohydride (278 mg, 7.34 mmol) was added. The obtained black suspension was sonicated for 30 min, and then a solution of compound 60 (2.40 g, 4.89 mmol, preparation reference: Chemical Communications 2010, 46, 6075-77) in MeOH (30 mL) and sodium borohydride (556 mg, 14.7 mmol) were added in successively. The reaction mixture was sonicated for 30 min, and then was filtered through a pad of celite. The filtrate was concentrated to remove the solvent. Water (100 mL) and DCM (200 mL) were added to the residue for extraction. The aqueous phase was extracted with DCM (100 mL×3), and the combined organic phase was washed with brine, dried, and concentrated. The residue was purified by silica gel chromatography (DCM/MeOH/TEA 100:4:1) to give a white foam-like solid 61 (1.73 g). LC-MS (Method 1): $R_t$=1.80 min; m/z (ES$^+$) 461.4 (M+H)$^+$.

Step 2

Both compound 61 (100 mg, 0.22 mmol) and compound 62 (110 mg, 0.33 mmol, preparation reference: Bioorganic and Medicinal Chemistry Letters 2007, 17, 501-506) were dissolved in DCM (3 mL), to which DIEA (152 μL, 0.87 mmol) and HATU (161 mg, 0.42 mmol) were sequentially added. The reaction mixture was stirred at rt for 2 h, and then concentrated to remove the solvent. The residue was purified by silica gel chromatography (PE/EtOAc 1:1→DCM/MeOH 25:1) to give a colorless oil 63 (158 mg). LC-MS (Method 2): $R_t$=2.26 min; m/z (ES$^+$) 779.5 (M+H)$^+$.

Step 3

Compound 63 (158 mg, 0.20 mmol) was dissolved in 1,4-dioxane (4 mL), to which conc. HCl (2 mL) was added. The reaction mixture was stirred at rt for 16 h, and then the solvent was removed by concentration. The crude product 64 was used directly for next step.

Step 4

Saturated sodium bicarbonate (2.5 mL) and THF (2.5 mL) were added to the crude compound 64 obtained from last step. The mixture was cooled to 0° C., to which N-(methoxycarbonyl)maleimide (158 mg, 1.02 mmol) was added in batches. The reaction mixture was stirred at 0° C. for 10 min, and then was stirred at rt for 3 h. Diluted HCl was added to the mixture to adjust pH to 2~3, and then the mixture was extracted with EtOAc (50 mL×2). The combined organic phase was dried and concentrated, and the residue was purified by silica gel chromatography (PE/EtOAc 1:1→DCM/MeOH 25:1) to give colorless oil 9 (10 mg). LC-MS (Method 1): $R_t$=1.52 min; m/z (ES$^+$) 663.3 (M+H)$^+$. $^1$H NMR (500 MHz, CDCl$_3$) δ6.80 (s, 1H), 6.71 (s, 6H), 4.04 (s, 2H), 3.78-3.72 (m, 6H), 3.65-3.61 (m, 14H), 2.59 (t, 2H), 2.13-2.10 (m, 6H).

EXAMPLE 10

Preparation of Compound 10

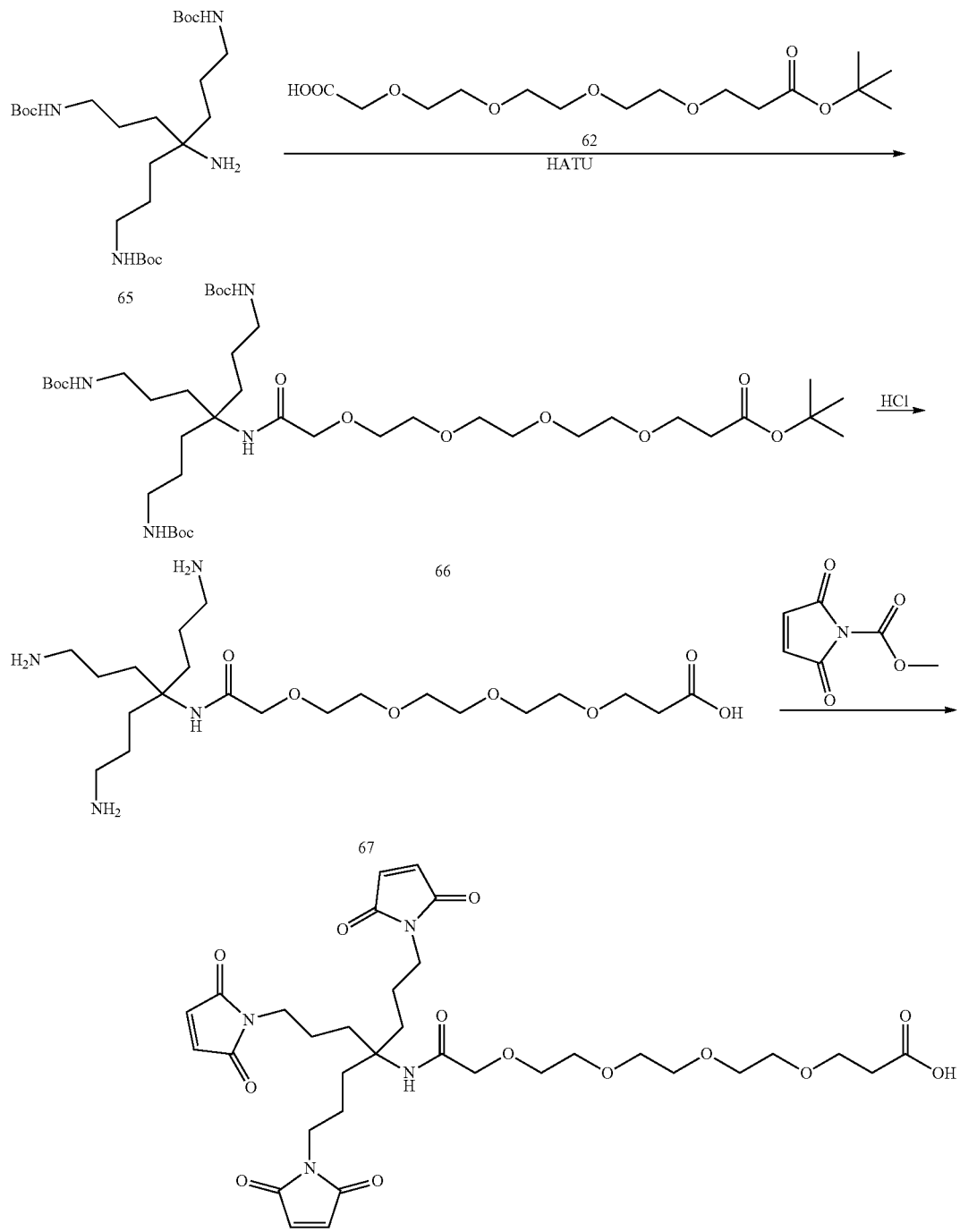

Step 1

Compound 65 (200 mg, 0.40 mmol, preparation reference: Journal of the American Chemical Society 2012, 134, 9898-9901) and compound 62 (202 mg, 0.60 mmol) were dissolved in DCM (6 mL), to which DIEA (180 μL, 0.16 mmol) and HATU (304 mg, 0.80 mmol) were added sequentially. The reaction mixture was stirred at rt for 2 h, and then the solvent was removed by concentratration. The residue was purified by silica gel chromatography (PE/EtOAC 1:1→DCM/MeOH 25:1) to give pale yellow oil 66 (200 mg). LC-MS (Method 2): $R_t$=2.30 min; m/z (ES$^+$) 838.5 (M+NH$_4$)$^+$.

Step 2, 3

Compound 66 (200 mg, 0.24 mmol) was dissolved in 1,4-dioxane (4 mL), to which conc. HCl (2 mL) was added. The reaction mixture was stirred at rt for 16 h, and then the solvent was removed by concentration. Saturated sodium bicarbonate (2.5 mL) and THF (2.5 mL) were added to the residue, and then the mixture was cooled to 0° C., to which N-(methoxycarbonyl)maleimide (189 mg, 1.22 mmol) was added in batches. The reaction mixture was stirred at 0° C. for 10 min, and then stirred at rt for 3 h. conc. HCl was added to the solution to adjust pH to 2-3, and then the mixture was extracted with EtOAc (50 mL×2). The combined organic phase was dried and concentrated, and the residue was purified by prep-RP-HPLC (Method 4: 20%-45% B in 8 min→95% B in 4 min) to give colorless oil 10 (5 mg). LC-MS (Method 2): $R_t$=1.50 min; m/z (ES$^+$) 703.0 (M−H)$^+$.

EXAMPLE 11

Preparation of Linker-Drug 5-vcMMAE

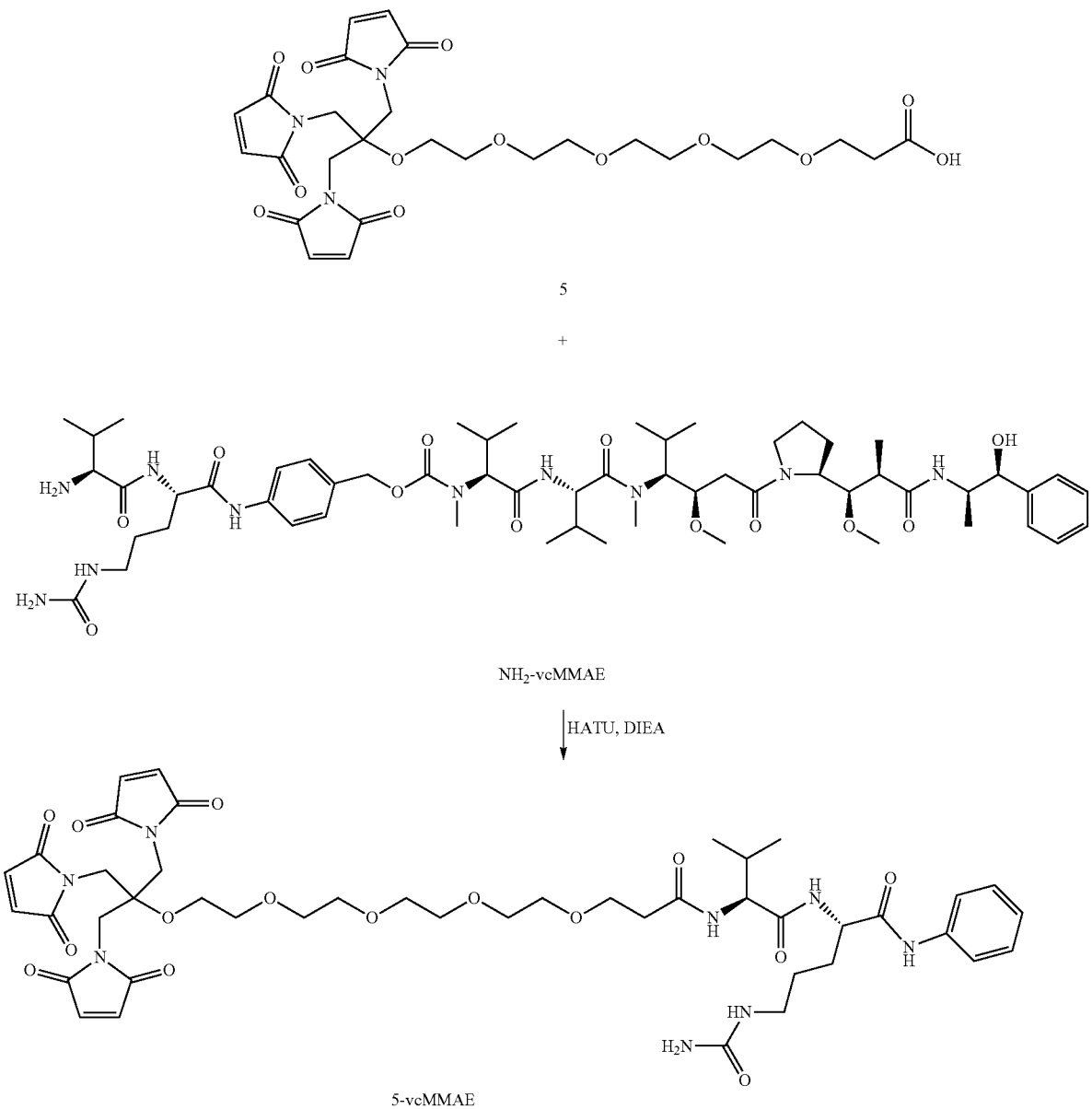

-continued

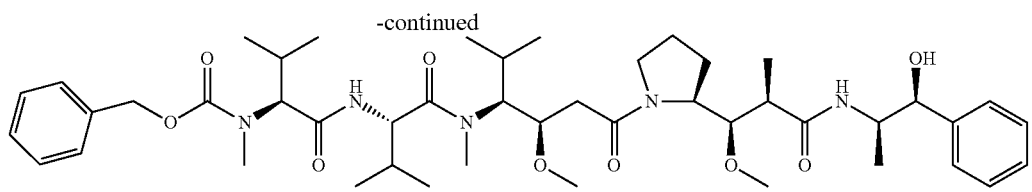

Compound 5 (20.0 mg, 32.9 µmol) and NH₂-vcMMAE (TFA salt, 25 mg, 20.2 µmol, preparation reference: WO 2013/173337) were dissolved in DMF (1.5 mL), to which DIEA (14.1 µL, 81.8 µmol) and HATU (15.4 mg, 40.4 µmol) were added. The reaction mixture was stirred at rt for 2 h, and then was purified by prep-RP-HPLC (Method 3: 40-60% B in 8 min→95% B in 4 min) to give a white solid 5-vcMMAE (29.5 mg). LC-MS (Method 1): $R_f$=1.89 min; m/z (ES⁺) 857.0 [½(M+2H)]⁺.

EXAMPLE 12

Other linker-drugs were synthesized in a similar way as that for 5-vcMMAE. Table 1 shows the LC-MS data for these products.

TABLE 1

LC-MS results for trimaleimide linker-vcMMAEs

| Compound | LC-MS Method; $R_f$ (min); m/z 1/2[M + 2H]⁺ |
|---|---|
| 1-vcMMAE | 1; 1.96; 762.5 |
| 2-vcMMAE | 1; 1.88; 776.0 |
| 3-vcMMAE | 1; 1.55; 782.4 |
| 4-vcMMAE | 1; 1.95; 768.2 |
| 6-vcMMAE | 1; 1.98; 864.5 |
| 7-vcMMAE | 1; 1.90; 804.2 |
| 8-vcMMAE | 1; 1.87; 790.1 |
| 9-vcMMAE | 1; 1.86; 884.8 |
| 10-vcMMAE | 1; 1.89; 905.7 |

EXAMPLE 13

Synthesis, Characterization, and Cell Proliferation Assay Results for the ADC Products Synthesis of ADC followed general procedure A. After purification, the ADC products were characterized/studied by SD S-PAGE (general procedure B), HIC (general procedure C), SEC (general procedure D), average DAR determination (general procedure E), native MS (general procedure F), ELISA (general procedure G), and cell proliferation assay (general procedure H).

Figure 5:
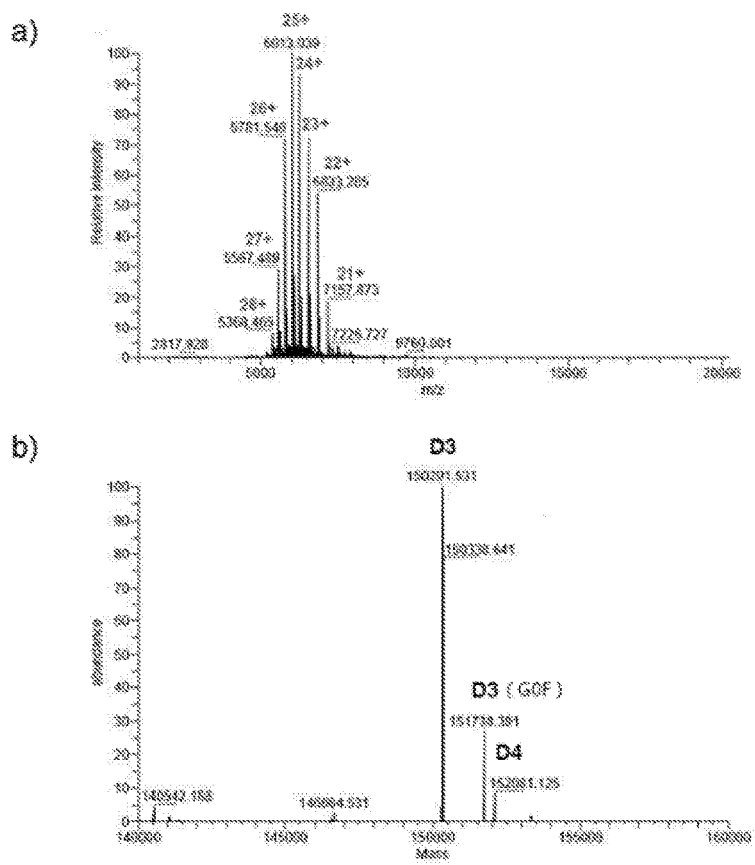
FIG. 5 illustrates the native MS results of antibody-drug conjugate of H-5-vcMMAE, wherein a is original MS data, b is deconvoluted MS spectra.
Figure 6:
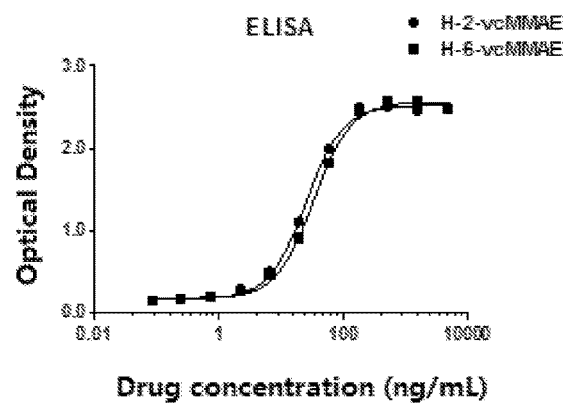
FIG. 6 illustrates the ELISA results of antibody-drug conjugate of H-trimaleimide linker-vcMMAE.
Figure 7:
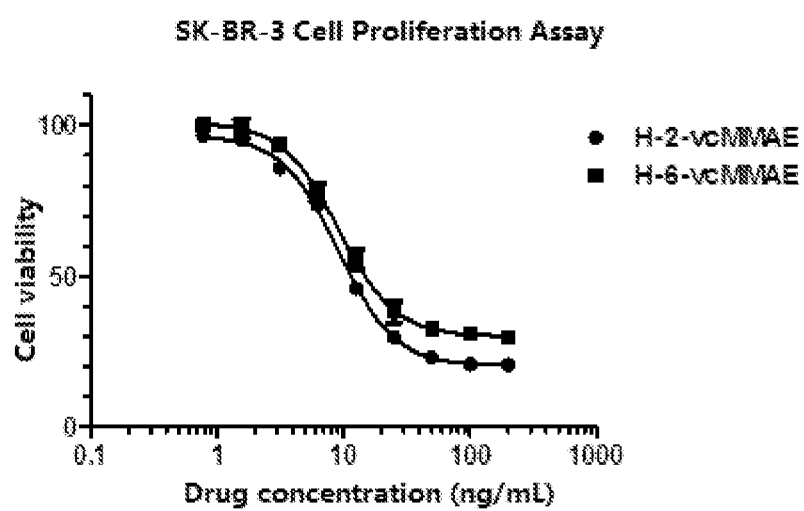
FIG. 7 illustrates the cell proliferation inhibition assay results of antibody-drug conjugate of H-trimaleimide linker-vcMMAE.

The average DAR results of the ADC products (Table 2) showed that the average DAR of the ADC products based on trimaleimide linkers of the invention could be easily controlled at around 3, due to that the trimaleimide linker of the invention could specifically controlled the conjugation sites and numbers. The native MS result (FIG. 5) of ADC H-5-vcMMAE also showed that the DAR 3 ADC is the main component (90%+).

TABLE 2

Average DAR

| ADC | Average DAR |
|---|---|
| H-1-vcMMAE | 3.1 |
| H-2-vcMMAE | 3.0 |
| H-3-vcMMAE | 2.9 |
| H-4-vcMMAE | 3.1 |
| H-5-vcMMAE | 3.1 |
| H-6-vcMMAE | 3.0 |
| H-7-vcMMAE | 3.0 |
| H-8-vcMMAE | 3.0 |
| H-9-vcMMAE | 3.4 |
| H-10-vcMMAE | 3.2 |

Table 3 showed the cell proliferation assay results.

TABLE 3

Cell Proliferation Assay Results

| ADC | IC₅₀ (ng/mL) |
|---|---|
| H-1-vcMMAE | 11.0 |
| H-2-vcMMAE | 9.0 |
| H-3-vcMMAE | 7.3 |
| H-4-vcMMAE | 10.6 |
| H-5-vcMMAE | 7.0 |
| H-6-vcMMAE | 9.3 |
| H-7-vcMMAE | 7.9 |
| H-8-vcMMAE | 9.3 |
| H-9-vcMMAE | 5.7 |
| H-10-vcMMAE | 6.9 |

All literatures mentioned in the present invention were cited as references, exactly the same as each literature was cited independently as reference. It should be noted that the present invention could be modified by those in the art, which is also within the scope of the claims of the present invention.

What is claimed is:

1. An antibody-drug conjugate of formula (I):

wherein L is an antibody, antibody fragment, or protein; T is a trimaleimide linker; A is other linker part; D is a drug moiety; n is an integer ranging from 1 to 8;

the trimaleimide linker of formula (II):

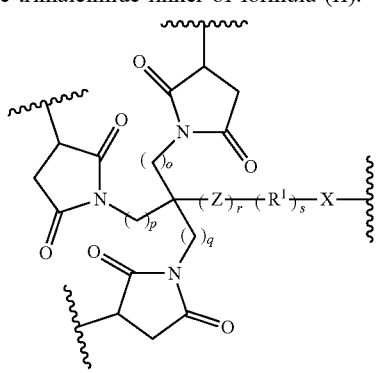

(II)

wherein

Z is selected from O, S, $NR^2$, $NR^3C(=O)$, $C(=O)NR^4$, $C(=O)O$, $OC(=O)$, $C(=S)O$, $OC(=S)$, $C(=S)NR^5$, $NR^6C(=S)$, $C(=S)S$, $SC(=S)$, $NR^7C(=O)NR^8$, $NR^9C(=S)NR^{10}$, $OC(=O)NR^{11}$ or $NR^{12}C(=O)O$;

$R^1$ is selected from alkylene, alkenlene, alkynlene, arylene, $-(CH_2CH_2O)_t-$, $-(OCH_2CH_2)_w-$, or any combination thereof, wherein t and w are independently selected from integers ranging from 1 to 18;

$R^2$, $R^3$, $R^4$, $R^5$, $R^6$, $R^7$, $R^8$, $R^9$, $R^{10}$, $R^{11}$ and $R^{12}$ are independently selected from H, alkyl, aryl, heterocyclyl, aryl, or heteroaryl;

r is selected from 0 or 1;

s is an integer ranging from 0 to 8;

X is selected from $NR^{13}$, O, S, $C(=O)$, $C(=S)$, $C(=O)NR^{14}$, $NR^{15}C(=O)$, $NR^{16}C(=S)$, $C(=S)NR^{17}$, $OC(=O)$, $C(=O)O$, $OC(=S)$, or $C(=S)O$; wherein $R^{13}$, $R^{14}$, $R^{15}$, $R^{16}$ and $R^{17}$ are independently selected from H, alkyl, aryl, heterocyclyl, arylalkyl or heteroarylalkyl;

o, p and q are integers independently selected from 0 to 8, wherein when one of them is set to zero, the others cannot be zero.

2. The antibody-drug conjugate of claim 1, wherein A is a cleavable linker group or a noncleavable linker.

3. The antibody-drug conjugate of claim 2, wherein A is represented by formula (III) or (IV):

$C-E_e-F_f$ (III)

$G_g$ (IV)

wherein C is a cleavable linker, E is a self-immolative linker; F is an optional self-immolative linker; e and f are independently selected from integers ranging from 0 to 5; G is a noncleavable linker; g is an integer ranging from 0 to 5.

4. The antibody-drug conjugate of claim 1, wherein the antibody-drug conjugate is represented by formula (V) or (VI):

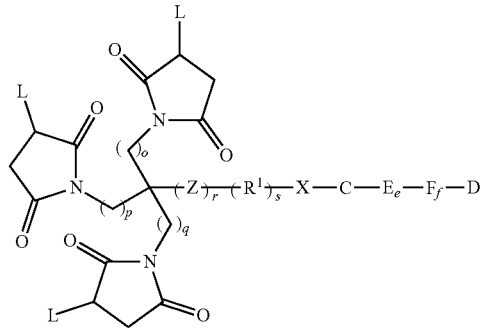

(V)

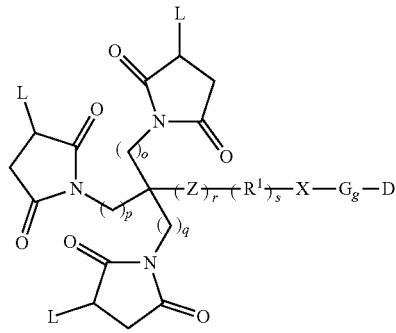

(VI)

wherein

L is an antibody, antibody fragment, or protein;

Z is selected from O, S, $NR^2$, $NR^3C(=O)$, $C(=O)NR^4$, $C(=O)O$, $OC(=O)$, $C(=S)O$, $OC(=S)$, $C(=S)NR^5$, $NR^6C(=S)$, $C(=S)S$, $SC(=S)$, $NR^7C(=O)NR^8$, $NR^9C(=S)NR^{10}$, $OC(=O)NR^{11}$, or $NR^{12}C(=O)O$;

$R^1$ is selected from alkylene, alkenlene, alkynlene, arylene, $-(CH_2CH_2O)_t-$, $-(OCH_2CH_2)_w-$, or any combination thereof, wherein t and w are independently selected from integers ranging from 1 to 18;

$R^2$, $R^3$, $R^4$, $R^5$, $R^6$, $R^7$, $R^8$, $R^9$, $R^{10}$, $R^{11}$ and $R^{12}$ are independently selected from H, alkyl, aryl, heterocyclyl, aryl, or heteroaryl;

r is selected from 0 or 1;

s is an integer ranging from 0 to 8;

X is selected from $NR^{13}$, O, S, $C(=O)$, $C(=S)$, $C(=O)NR^{14}$, $NR^{15}C(=O)$, $NR^{16}C(=S)$, $C(=S)NR^{17}$, $OC(=O)$, $C(=O)O$, $OC(=S)$, or $C(=S)O$; wherein $R^{13}$, $R^{14}$, $R^{15}$, $R^{16}$ and $R^{17}$ are independently selected from H, alkyl, aryl, heterocyclyl, arylalkyl, or heteroarylalkyl;

o, p and q are integers independently selected from 0 to 8, wherein when one of them is set to zero, the others cannot be zero.

5. The antibody-drug conjugate of claim 1, wherein the antibody targets cell surface receptors or tumor-related antigens.

6. The antibody-drug conjugate of claim 1, wherein the drug is cytotoxic drug, anti-autoimmune disease drug, or anti-inflammation drug.

7. The antibody-drug conjugate of claim 1, wherein the trimaleimide linker is formed by reacting one of the following formulae with another linker part-drug moiety, followed by conjugation with an antibody, antibody fragment, protein, protein fragment or polypeptide:

| Compound | No. |
|---|---|
| 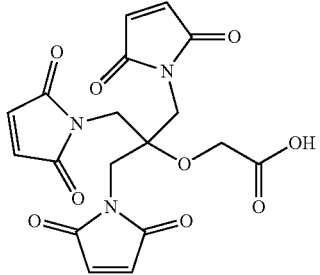 [SMILES: O=C(O)COC(CN1C(=O)C=CC1=O)(CN1C(=O)C=CC1=O)CN1C(=O)C=CC1=O] | 1 |
| 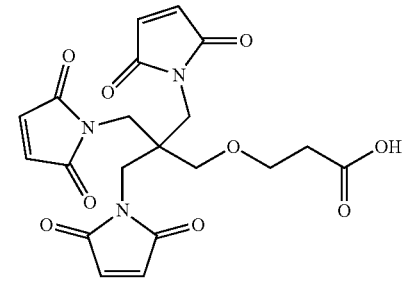 [SMILES: O=C(O)CCOCC(CN1C(=O)C=CC1=O)(CN1C(=O)C=CC1=O)CN1C(=O)C=CC1=O] | 2 |
| 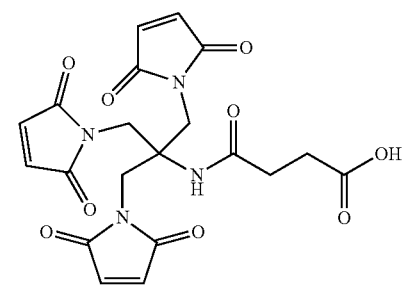 [SMILES: O=C(O)CCC(=O)NC(CN1C(=O)C=CC1=O)(CN1C(=O)C=CC1=O)CN1C(=O)C=CC1=O] | 3 |
| 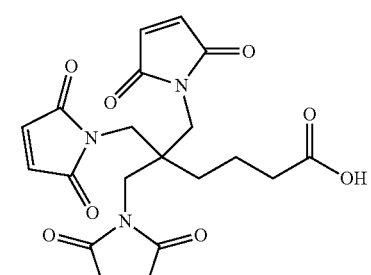 | 4 |
| 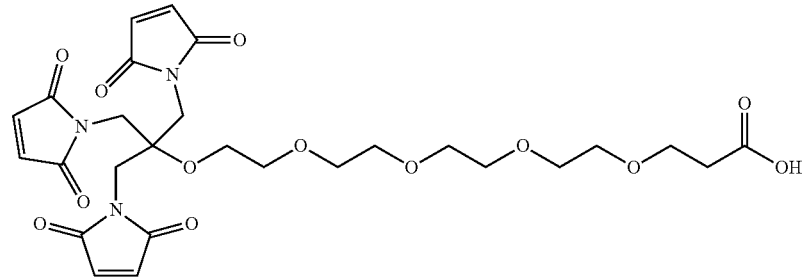 [SMILES: O=C(O)CCOCCOCCOCCOCCOC(CN1C(=O)C=CC1=O)(CN1C(=O)C=CC1=O)CN1C(=O)C=CC1=O] | 5 |

-continued
| Compound | No. |
|---|---|
| 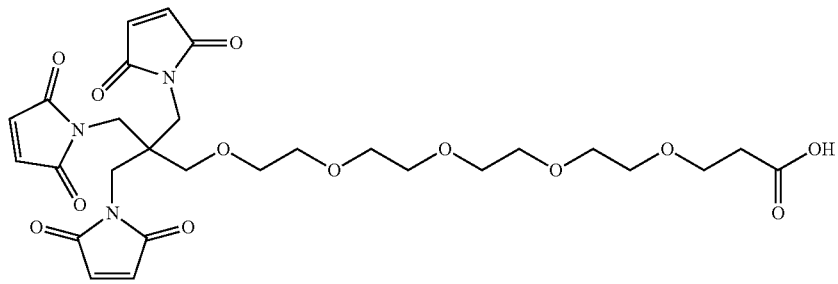 [SMILES: O=C(O)CCOCCOCCOCCOCCOCC(CN1C(=O)C=CC1=O)(CN1C(=O)C=CC1=O)CN1C(=O)C=CC1=O] | 6 |
| 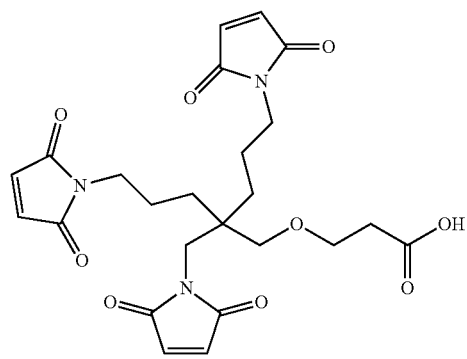 [SMILES: O=C(O)CCOCC(CCCN1C(=O)C=CC1=O)(CCCN1C(=O)C=CC1=O)CN1C(=O)C=CC1=O] | 7 |
| 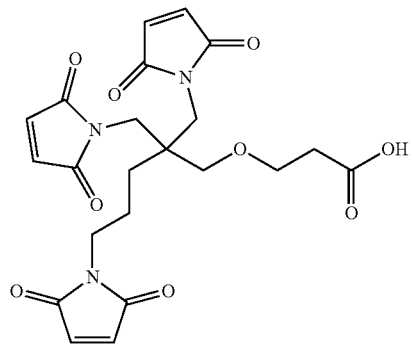 [SMILES: O=C(O)CCOCC(CCCN1C(=O)C=CC1=O)(CN1C(=O)C=CC1=O)CN1C(=O)C=CC1=O] | 8 |
| 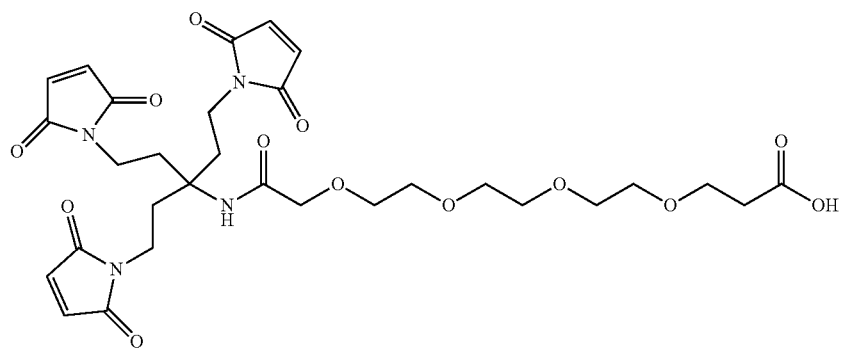 [SMILES: O=C(O)CCOCCOCCOCCOCC(=O)NC(CCN1C(=O)C=CC1=O)(CCN1C(=O)C=CC1=O)CCN1C(=O)C=CC1=O] | 9 |

| Compound | No. |
|---|---|
|  | 10 |

8. Use of a trimaleimide linker of formula (VII) for the manufacturing of an antibody-drug conjugate:

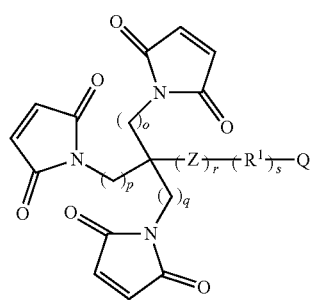
(VII)

wherein Z is selected from O, S, $NR^2$, $NR^3C(=O)$, $C(=O)NR^4$, $C(=O)O$, $OC(=O)$, $C(=S)O$, $OC(=S)$, $C(=S)NR^5$, $NR^6C(=S)$, $C(=S)S$, $SC(=S)$, $NR^7C(=O)NR^8$, $NR^9C(=S)NR^{10}$, $OC(=O)NR^{11}$, or $NR^{12}C(=O)O$;

$R^1$ is selected from alkylene, alkenlene, alkynlene, arylene, $-(CH_2CH_2O)_t-$, $-(OCH_2CH_2)_w-$, or any combination thereof, wherein t and w are independently selected from integers ranging from 1 to 18;

$R^2$, $R^3$, $R^4$, $R^5$, $R^6$, $R^7$, $R^8$, $R^9$, $R^{10}$, $R^{11}$ and $R^{12}$ are independently selected from H, alkyl, aryl, heterocyclyl, arylalkyl, or heteroarylalkyl;

r is selected from 0 or 1;

s is an integer ranging from 0 to 8;

Q is selected from $NHR^{13}$, OH, SH, COOH, $C(=S)OH$, $NR^{14}COOH$, $NR^{15}C(=S)OH$, NCO, or NCS, wherein $R^{13}$, $R^{14}$, and $R^{15}$ are independently selected from H, alkyl, aryl, heterocyclyl, arylalkyl, or heteroarylalkyl;

o, p and q are integers independently selected from 0 to 8, wherein when one of them is set to zero, the other two cannot be zero, wherein the use of a trimaleimide linker of formula (VII) comprises the step of adding a pharmaceutically effective amount of the trimaleimide linker of formula (VII) to react with an antibody, antibody fragment, protein, protein fragment or polypeptide to form the antibody-drug conjugate.

9. The use of the claim 8, wherein the trimaleimide linker has one of the following formulae

| Compound | No. |
|---|---|
| 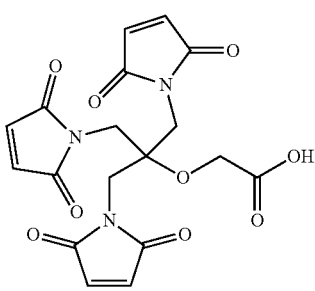 [SMILES: O=C(O)COC(CN1C(=O)C=CC1=O)(CN1C(=O)C=CC1=O)CN1C(=O)C=CC1=O] | 1 |

| Compound | No. |
|---|---|
| | 2 |
| | 3 |
| | 4 |
| | 5 |
| | 6 |

-continued

| Compound | No. |
|---|---|
| (structure) | 7 |
| (structure) | 8 |
| (structure) | 9 |
| (structure) | 10 |

* * * * *